(12) United States Patent
Yoo et al.

(10) Patent No.: US 9,151,988 B2
(45) Date of Patent: Oct. 6, 2015

(54) CYCLIC OLEFIN COMPOUND, PHOTOREACTIVE POLYMER, AND ALIGNMENT LAYER COMPRISING THE SAME

(71) Applicant: LG CHEM, LTD., Seoul (KR)

(72) Inventors: Dong-Woo Yoo, Daejeon (KR); Sung-Ho Chun, Daejeon (KR); Dai-Seung Choi, Daejeon (KR); Sung-Kyoung Lee, Seoul (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/567,823

(22) Filed: Dec. 11, 2014

(65) Prior Publication Data

US 2015/0093520 A1 Apr. 2, 2015

(30) Foreign Application Priority Data

Sep. 27, 2010 (KR) ................. 10-2010-0093180
Jun. 7, 2011 (KR) ................. 10-2011-0054322

(51) Int. Cl.
| | |
|---|---|
| G02F 1/1337 | (2006.01) |
| C08F 32/04 | (2006.01) |
| C08F 32/08 | (2006.01) |
| C08G 61/08 | (2006.01) |
| C07C 69/734 | (2006.01) |
| C07C 69/738 | (2006.01) |
| C08F 20/40 | (2006.01) |

(52) U.S. Cl.
CPC ........ *G02F 1/133711* (2013.01); *C07C 69/734* (2013.01); *C07C 69/738* (2013.01); *C08F 20/40* (2013.01); *C08F 32/08* (2013.01); *C08G 61/08* (2013.01); *C07C 2102/42* (2013.01); *C08G 2261/135* (2013.01); *C08G 2261/148* (2013.01); *C08G 2261/1414* (2013.01); *C08G 2261/1426* (2013.01); *C08G 2261/3324* (2013.01); *C08G 2261/418* (2013.01); *C08G 2261/76* (2013.01); *G02F 1/133788* (2013.01); *Y10S 525/94* (2013.01); *Y10T 428/1005* (2015.01); *Y10T 428/31855* (2015.04)

(58) Field of Classification Search
USPC ........... 428/1.2; 526/256, 259, 266, 274, 282; 525/326.7, 327.2, 332.1
See application file for complete search history.

(56) References Cited

U.S. PATENT DOCUMENTS

| | | | |
|---|---|---|---|
| 5,464,669 A | 11/1995 | Kang et al. | |
| 2006/0159865 A1 | 7/2006 | Kim et al. | |
| 2010/0047481 A1 | 2/2010 | Choi et al. | |
| 2010/0068419 A1 | 3/2010 | Kim | |
| 2010/0093955 A1 | 4/2010 | Choi | |
| 2010/0121005 A1 | 5/2010 | Kim et al. | |
| 2010/0182547 A1 | 7/2010 | Ryu et al. | |

FOREIGN PATENT DOCUMENTS

| | | |
|---|---|---|
| CN | 1340592 A | 3/2002 |
| CN | 1659205 | 8/2005 |
| CN | 1881020 | 12/2006 |
| CN | 1881020 A | 12/2006 |
| CN | 101065342 | 10/2007 |
| CN | 101098840 | 1/2008 |
| CN | 100396756 | 6/2008 |
| CN | 101558131 | 10/2009 |
| CN | 101558131 A | 10/2009 |
| CN | 101641389 | 2/2010 |
| CN | 101671250 | 3/2010 |
| EP | 1188746 | 3/2002 |
| EP | 2390690 | 11/2011 |
| JP | 11181127 | 7/1999 |
| JP | 2001200018 | 7/2001 |
| JP | 2010080010 | 7/2001 |
| JP | 2003048998 | 2/2003 |
| JP | 2003306468 | 10/2003 |
| JP | 2010164975 | 7/2010 |
| JP | 2010522253 | 7/2010 |
| JP | 2011510345 | 3/2011 |
| JP | 2011511957 | 4/2011 |
| JP | 2011514542 | 5/2011 |
| KR | 1020020006819 | 1/2002 |
| KR | 1020040099406 | 11/2004 |
| KR | 100536824 | 12/2005 |
| KR | 100671753 | 1/2007 |
| KR | 100789247 | 12/2007 |
| KR | 1020080073168 | 8/2008 |
| KR | 1020080086409 | 9/2008 |
| KR | 10-2008-0095207 A | 10/2008 |
| KR | 10-2009-0047720 A | 5/2009 |
| KR | 1020090047720 | 5/2009 |
| KR | 1020090079842 | 7/2009 |
| KR | 1020090079843 | 7/2009 |
| KR | 1020090079844 | 7/2009 |

(Continued)

OTHER PUBLICATIONS

Machine translation of KR 1020090047720, published May 2009.*
Martin Schadt et al., "Surface-Induced Parallel Alignment of Liquid Crystals by Linearly Polymerized Photopolymers", Jpn. J. Appl. Phys., vol. 31 (1992), pp. 2155-2164 Part 1, No. 7, Jul. 1992.
Andrey Dyaduysha et al., "Peculiarity of an Oblique Liquid Crystal Alignment Induced by a Photosensitive Orientant", Jpn. J. Appl. Phys., vol. 34 (1995), pp. 1000-1002, Part 2, No. 8A, Aug. 1, 1995.
Arvind Kumar et al., "Photopatterned electrochromic conjugated polymer films via precursor approach", Polymer 49 (2008), pp. 3686-3692.

*Primary Examiner* — Fred M Teskin
(74) *Attorney, Agent, or Firm* — Dentons US LLP

(57) ABSTRACT

Disclosed herein are a cyclic olefin compound, a photoreactive polymer, and an alignment layer comprising the photoreactive polymer, where the cyclic olefin compound can be used to provide the photoreactive polymer having not only excellences in liquid crystal alignment and alignment rate but also readiness for change in the alignment direction depending on the polarization direction.

6 Claims, 2 Drawing Sheets

(56) References Cited

FOREIGN PATENT DOCUMENTS

| KR | 1020100021751 | 2/2010 |
| KR | 1020110025377 | 3/2011 |
| KR | 1020100083103 | 7/2012 |
| KR | 101195186 | 10/2012 |
| WO | 9733198 | 9/1997 |
| WO | 2007142458 | 12/2007 |
| WO | 2009091225 | 7/2009 |

* cited by examiner

US 9,151,988 B2

CYCLIC OLEFIN COMPOUND, PHOTOREACTIVE POLYMER, AND ALIGNMENT LAYER COMPRISING THE SAME

This application is a divisional application of U.S. Pat. application Ser. No. 13/244,089, filed Sept. 23, 2011, now issued U.S. Pat. No. 8,946,366, and claims the benefit of Korean Patent Application Nos. 10-2010-0093180, filed on Sept. 27, 2010, and 10-2011-0054322, filed on Jun. 2011, which are hereby incorporated by reference in there entirety for all purposes as if fully set forth herein.

FIELD OF THE INVENTION

The present invention relates to a cyclic olefin compound, a photoreactive polymer, and an alignment layer comprising the same and, more particularly, to a cyclic olefin compound, a photoreactive polymer, a preparation method for the same, and an alignment layer comprising the photoreactive polymer, where the cyclic olefin compound can be used to provide the photoreactive polymer having not only excellences in liquid crystal alignment and alignment rate but also readiness for change in the alignment direction depending on the polarization direction.

BACKGROUND ART

With a recent advent of large-sized LCDs and a gradual expansion of their usage from portable devices, such as mobile phones, lap-top computers, etc., to home appliances, such as wall mounted flat panel TVs, there is a demand for LCDs with high definition and wide viewing angle. In particular, TFT-driven thin film transistor LCDs (TFT-LCDs) of which each pixel is independently driven are much superior in response speed of liquid crystals, realizing high-definition motion pictures, and thus increasingly used in a wider range of applications.

To be used as an optical switch in the TFT-LCDs, liquid crystals are required to be initially aligned in a defined direction on a layer including innermost TFT of the display cell. For this, a liquid crystal alignment layer is used.

For the liquid crystal alignment to occur, a heat-resistant polymer such as polyimide is applied on a transparent glass to form a polymer alignment layer, which is then subjected to a rubbing process using a rotary roller wound with a rubbing cloth of nylon or rayon fabrics at a high rotation speed to align liquid crystals.

However, the rubbing process remains mechanical scratches on the surface of the liquid crystal alignment layer or generates strong static electricity, possibly destroying the TFTs. Further, fine fibers coming from the rubbing cloth may cause defectives, which become an obstacle to acquiring a higher production yield.

To overcome the problems with the rubbing process and achieve innovation in the aspect of production yield, there has been derived a liquid crystal alignment method using a light such as UV radiation (hereinafter, referred to as "photo-alignment").

Photo-alignment refers to the mechanism using a linearly polarized UV radiation to cause the photoreactive groups of a defined photoreactive polymer to participate in a photoreaction, aligning the main chain of the polymer in a defined direction to form a photo-polymerized liquid crystal alignment layer with aligned liquid crystals.

The representative example of the photo-alignment is photopolymerization-based photo-alignment as disclosed by M. Schadt et al. (Jpn. J. Appl. Phys., Vol 31., 1992, 2155), Dae S. Kang et al. (U.S. Pat. No. 5,464,669), and Yuriy Reznikov (Jpn. J. Appl. Phys. Vol. 34, 1995, L1000). The photo-aligned polymers used in these patent and research papers are mostly polycinnamate-based polymers, such as poly(vinylcinnamate) (PVCN) or poly(vinyl methoxycinnamate) (PVMC). For photo-alignment of polymers, the double bond of cinnamate exposed to UV radiation participates in a [2+2] cycloaddition reaction to form cyclobutane, which provides anisotropy to cause liquid crystal molecules aligned in one direction, inducing liquid crystal alignment.

Besides, JP11-181127 discloses a polymer and an alignment layer including the same in which the polymer has a side chain including photoreactive groups such as cinnamate on a main chain such as acrylate, methacrylate, etc. Korean Patent Laid-Open Publication No. 2002-0006819 also discloses the use of an alignment layer comprising a polymethacryl-based polymer.

However, the above-mentioned conventional photoreactive polymers for alignment layer have a low thermal stability of the polymer main chain, undesirably deteriorating the stability of the alignment layer or providing poor characteristics in regard to photoreactivity, liquid crystal alignment, or alignment rate.

There are used patterned retarders, patterned cell alignment layers, or the like in the field of applications that uniquely require a change in the anisotropic direction depending on the polarization direction to create three-dimensional stereoscopic images. But the conventional photoreactive polymers do not have a change in the alignment direction already determined by a polarized radiation and, if any, require a greater amount of radiation polarized in a different direction.

SUMMARY OF THE INVENTION

The present invention provides a cyclic olefin compound used to prepare a photoreactive polymer having not only excellences in liquid crystal alignment and alignment rate but also readiness for change in the alignment direction depending on the polarization direction.

Further, the present invention provides a photoreactive polymer and a preparation method for the same, where the photoreactive polymer has not only excellences in liquid crystal alignment and alignment rate but also readiness for change in the alignment direction depending on the polarization direction.

The present invention also provides an alignment layer and a display device that comprise the photoreactive polymer.

The present invention provides a cyclic olefin compound having a photoreactive group as represented by the following formula 1:

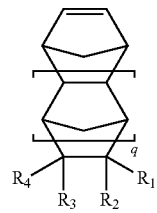

[Formula 1]

In the formula 1, q is an integer from 0 to 4; and at least one of R1, R2, R3 and R4 is any one selected from the group consisting of radicals of the following formula 1a or 1b.

Among the R1 to R4, the remainders other than the radical of the formula 1a or 1b are the same as or different from one another and independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; and a polar functional group comprising at least one of oxygen, nitrogen, phosphor, sulfur, silicon, and boron. When the R1 to R4 are not hydrogen, halogen, or a polar functional group, at least one of a R1 and R2 coordination and a R3 and R4 coordination is bonded to each other to form an alkylidene group having 1 to 10 carbon atoms; or R1 or R2 is bonded to either R3 or R4 to form a saturated or unsaturated aliphatic ring having 4 to 12 carbon atoms or an aromatic ring having 6 to 24 carbon atoms.

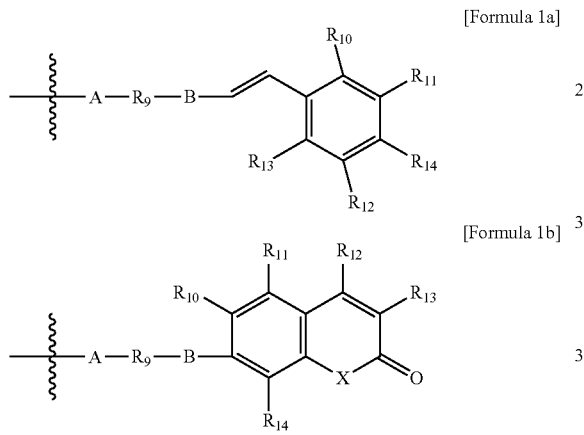

[Formula 1a]

[Formula 1b]

In the formula 1a or 1b, A is chemical bond, oxygen, sulfur, or —NH—. B is selected from the group consisting of chemical bond, substituted or unsubstituted alkylene having 1 to 20 carbon atoms, carbonyl, carboxy, ester, substituted or unsubstituted arylene having 6 to 40 carbon atoms, and substituted or unsubstituted heteroarylene having 6 to 40 carbon atoms. X is oxygen or sulfur. R9 is selected from the group consisting of chemical bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted aralkylene having 7 to 15 carbon atoms, and substituted or unsubstituted alkynylene having 2 to 20 carbon atoms. At least one of R10 to R14 is a radical represented by -L-R15-R16-(substituted or unsubstituted C6-C40 aryl). Among the R10 to R14, the remainders other than the radical of -L-R15-R16-(substituted or unsubstituted C6-C40 aryl) are the same as or different from one another and independently selected from the group consisting of hydrogen; halogen; substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; and heteroaryl having 6 to 40 carbon atoms with a hetero element in Group 14, 15 or 16. L is selected from the group consisting of oxygen, sulfur, —NH—, substituted or unsubstituted alkylene having 1 to 20 carbon atoms, carbonyl, carboxy, —CONH—, and substituted or unsubstituted arylene having 6 to 40 carbon atoms. R15 is substituted or unsubstituted alkyl having 1 to 10 carbon atoms. R16 is selected from the group consisting of chemical bond, —O—, —C(=O)O—, —OC(=O)—, —NH—, —S—, and —C(=O)—.

The present invention also provides a photoreactive polymer comprising a repeating unit of the following formula 3a or 3b:

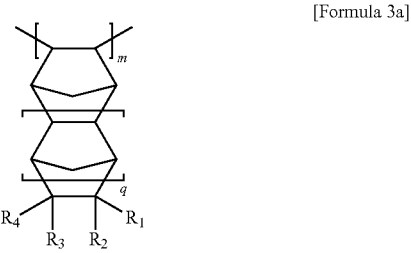

[Formula 3a]

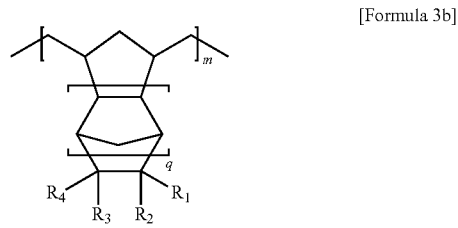

[Formula 3b]

In the formulas 3a and 3b, independently, m is 50 to 5,000; and q and R1 to R4 are as defined in the formula 1.

The present invention also provides a method for preparing a photoreactive polymer comprising a repeating unit of the formula 3a, which method comprises performing an addition polymerization reaction using a monomer represented by the following formula 1 in the presence of a catalyst composition comprising a precatalyst containing a transition metal in Group 10 and a cocatalyst to form the repeating unit of the formula 3a:

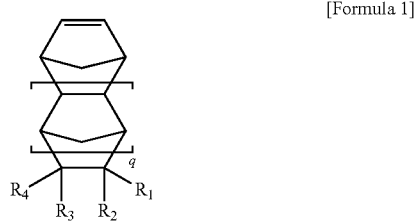

[Formula 1]

In the formulas 1, q and R1 to R4 are as defined above.

The present invention also provides a method for preparing a photoreactive polymer comprising a repeating unit of the formula 3b, which method comprises performing a ring-opening polymerization reaction using a monomer represented by the following formula 1 in the presence of a catalyst composition comprising a precatalyst containing a transition metal in Group 4, 6 or 8 and a cocatalyst to form the repeating unit of the formula 3b.

The present invention also provides an alignment layer comprising the photoreactive polymer.

The present invention also provides a liquid crystal retardation film that comprises the alignment layer and a liquid crystal layer on the alignment layer.

The present invention also provides a display device comprising the alignment layer.

The photoreactive polymer obtained from the cyclic olefin compound of the present invention has the end of its photoreactive group being bonded to a bulky substituent including aralkyl. The existence of the bulky substituent allows the photoreactive polymer far superior in liquid crystal alignment and alignment rate to the existing photoreactive polymers.

The photoreactive polymer contains photoreactive groups freely movable, so the alignment direction is considerably flexible depending on the polarization direction. With this characteristic, the photoreactive polymer and the alignment layer comprising the photoreactive polymer can be preferably applied to patterned retarders, patterned cell alignment layers, etc. used to realize three-dimensional images.

Accordingly, the photoreactive polymer can be preferably used as a photo-aligned polymer in various coating compositions and alignment layers formed from the coating compositions applicable to various LCD devices, and the alignment layer comprising the photoreactive polymer has excellent characteristics.

DETAILED DESCRIPTION OF THE PREFERRED EMBODIMENT

Figure 1:
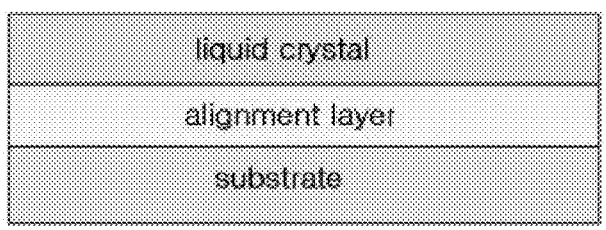
FIG. 1 is a schematic diagram showing an exemplary structure of a general alignment layer.

Hereinafter, a detailed description will be given as to a cyclic olefin compound, a photoreactive polymer, a preparation method for the same, and an alignment layer according to the embodiments of the invention.

In accordance with an embodiment of the invention, there is provided a cyclic olefin compound having a photoreactive group as represented by the following formula 1:

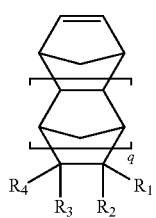

[Formula 1]

In the formula 1, q is an integer from 0 to 4; and at least one of $R_1$, $R_2$, $R_3$ and $R_4$ is any one selected from the group consisting of radicals of the following formula 1a and 1b. Among the $R_1$ to $R_4$, the remainders other than the radical of the formula 1a or 1b are the same as or different from one another and independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; and a polar functional group comprising at least one of oxygen, nitrogen, phosphor, sulfur, silicon, and boron. When the $R_1$ to $R_4$ are not hydrogen, halogen, or a polar functional group, at least one of a $R_1$ and $R_2$ coordination and a $R_3$ and $R_4$ coordination is bonded to each other to form an alkylidene group having 1 to 10 carbon atoms; or $R_1$ or $R_2$ is bonded to either $R_3$ or $R_4$ to form a saturated or unsaturated aliphatic ring having 4 to 12 carbon atoms or an aromatic ring having 6 to 24 carbon atoms.

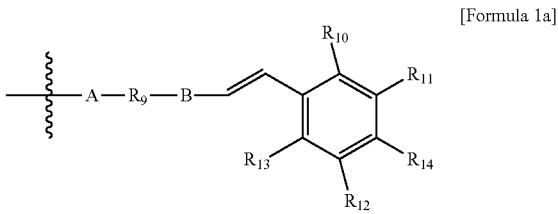

[Formula 1a]

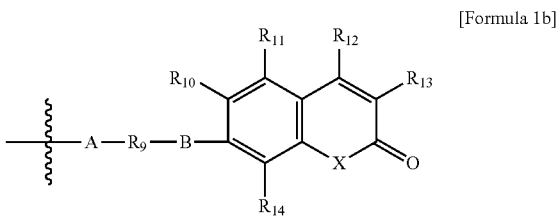

[Formula 1b]

In the formula 1a or 1b, A is chemical bond, oxygen, sulfur, or —NH—. B is selected from the group consisting of chemical bond, substituted or unsubstituted alkylene having 1 to 20 carbon atoms, carbonyl, carboxy, ester, substituted or unsubstituted arylene having 6 to 40 carbon atoms, and substituted or unsubstituted heteroarylene having 6 to 40 carbon atoms. X is oxygen or sulfur. $R_9$ is selected from the group consisting of chemical bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted aralkylene having 7 to 15 carbon atoms, and substituted or unsubstituted alkynylene having 2 to 20 carbon atoms. At least one of $R_{10}$ to $R_{14}$ is a radical represented by -L-$R_{15}$-$R_{16}$-(substituted or unsubstituted C6-C40 aryl). Among the $R_{10}$ to $R_{14}$, the remainders other than the radical of -L-$R_{15}$-$R_{16}$-(substituted or unsubstituted C6-C40 aryl) are the same as or different from one another and independently selected from the group consisting of hydrogen; halogen; substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; and heteroaryl having 6 to 40 carbon atoms with a hetero element in Group 14, 15 or 16. L is selected from the group consisting of oxygen, sulfur, —NH—, substituted or unsubstituted alkylene having 1 to 20 carbon atoms, carbonyl, carboxy, —CONH—, and substituted or unsubstituted arylene having 6 to 40 carbon atoms. $R_{15}$ is substituted or unsubstituted alkyl having 1 to 10 carbon atoms. $R_{16}$ is selected from the group consisting of chemical bond, —O—, —C(=O)O—, —OC(=O)—, —NH—, —S—, and —C(=O)—.

In such a cyclic olefin compound, the radical of -L-R15-R16-(substituted or unsubstituted C6-C40 aryl) is represented by the following formula 2:

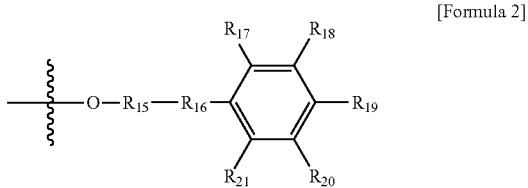

[Formula 2]

In the formula 2, R15 and R16 are as defined in formula 1; and R17 to R21 are the same as or different from one another and independently selected from the group consisting of hydrogen; halogen; substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; heteroaryl having 6 to 40 carbon atoms with a hetero element in Group 14, 15 or 16; and substituted or unsubstituted alkoxyaryl having 6 to 40 carbon atoms.

Such a compound has a chemical structure in which the ends of photoreactive groups such as cinnamate are bonded to a substituent represented by -L-R15-R16-(substituted or unsubstituted C6-C40 aryl). The substituent comprises an aralkyl structure that alkyl and aryl groups are sequentially connected together via a linker L. Such a bulky chemical structure as aralkyl is connected to the ends of photoreactive groups via a linker L, confirming the formation of a large free volume between the photoreactive groups. This seems likely to be caused by the steric hindrance between adjacent bulky aralkyl structures.

For this reason, photoreactive groups such as cinnamate in the photoreactive polymer and the alignment layer prepared using the cyclic olefin compound are relatively free to move (flow) or react in such a large free volume, minimizing hindrance from other reactors or substituents. Consequently, the photoreactive groups in the photoreactive polymer and the alignment layer can have excellences in photoreactivity, alignment rate, and photo-alignment. Especially, photoreactive groups such as cinnamate undergo photo-alignment, which takes place as a simultaneous occurrence of dimerization and isomerization caused by polarized radiation. The photo-alignment occurs more easily and rapidly without any hindrance in the large free volume. Accordingly, the photoreactive polymer and the alignment layer prepared from the cyclic olefin compound are enabled to have better excellences in photoreactivity, alignment, and alignment rate.

In the photoreactive polymer and the alignment layer, the existence of the large free volume between adjacent photoreactive groups allows the photoreactive groups relatively free to change the alignment direction depending on the change in the polarization direction. Consequently, the alignment direction may be easily changed according to the polarization direction, and the photoreactive polymer can be preferably applied to patterned retarders, patterned cell alignment layers, or the like that are used to create stereoscopic images.

With a recent demand for wide viewing angles, there have been many attempts to substitute photo-alignment layers for TFT-cell alignment layers and pattern liquid crystals through multidirectional patterning to realize wide viewing angles. As for the conventional alignment layers of which the alignment direction is dependent upon the polarization direction, it is necessary to carry out a patterning process using two masks when a pattern of the specific direction is required. In contrast, as for the photoreactive polymer and the alignment layer comprising the photoreactive polymer according to the embodiment, the alignment direction even after exposure to polarized radiation of a specific direction can be changed again by polarized radiation of a different direction, realizing a desired alignment layer through a single-mask process.

As a result, the cyclic olefin compound possesses not only excellences in liquid crystal alignment and alignment rate but also readiness for change in the alignment direction depending on the polarization direction, thereby providing a photoreactive polymer applicable to various alignment layers.

Hereinafter, a further detailed description will be given as to the cyclic olefin compound and the photoreactive polymer obtained from the same.

In the cyclic olefin compound, a polar functional group used as a substituent for the R1 to R4, that is, a polar functional group including at least one of oxygen, nitrogen, phosphor, sulfur, silicon, and boron may be selected from the group consisting of the following functional groups, or otherwise, comprise at least one of oxygen, nitrogen, phosphor, sulfur, silicon, and boron:

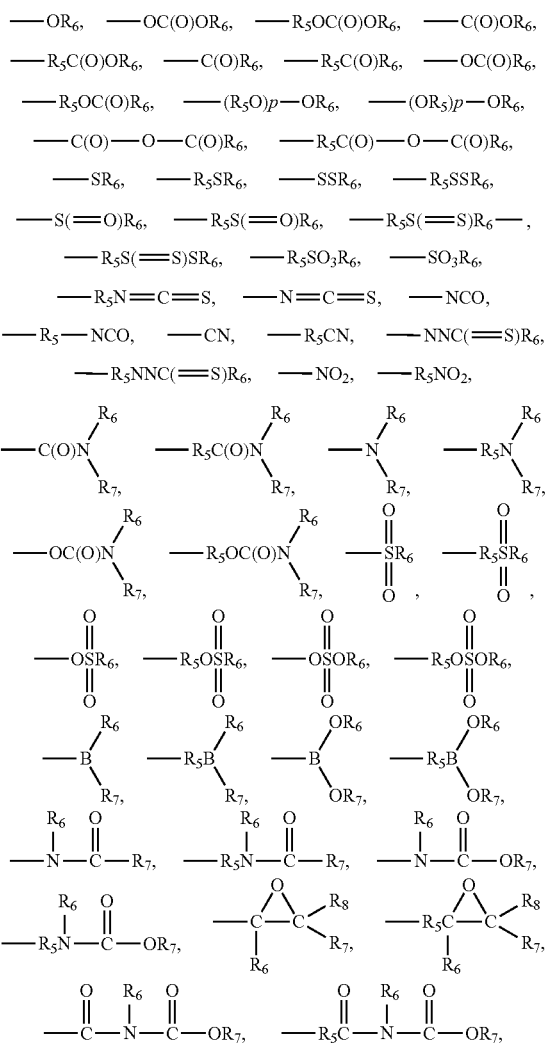

-continued

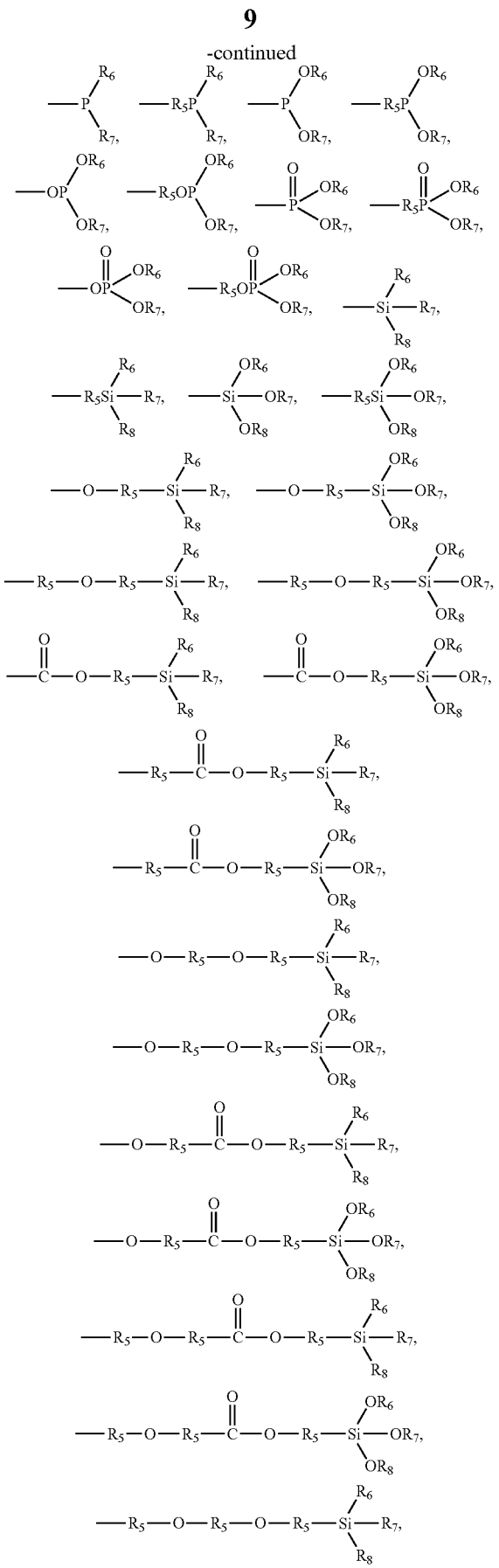

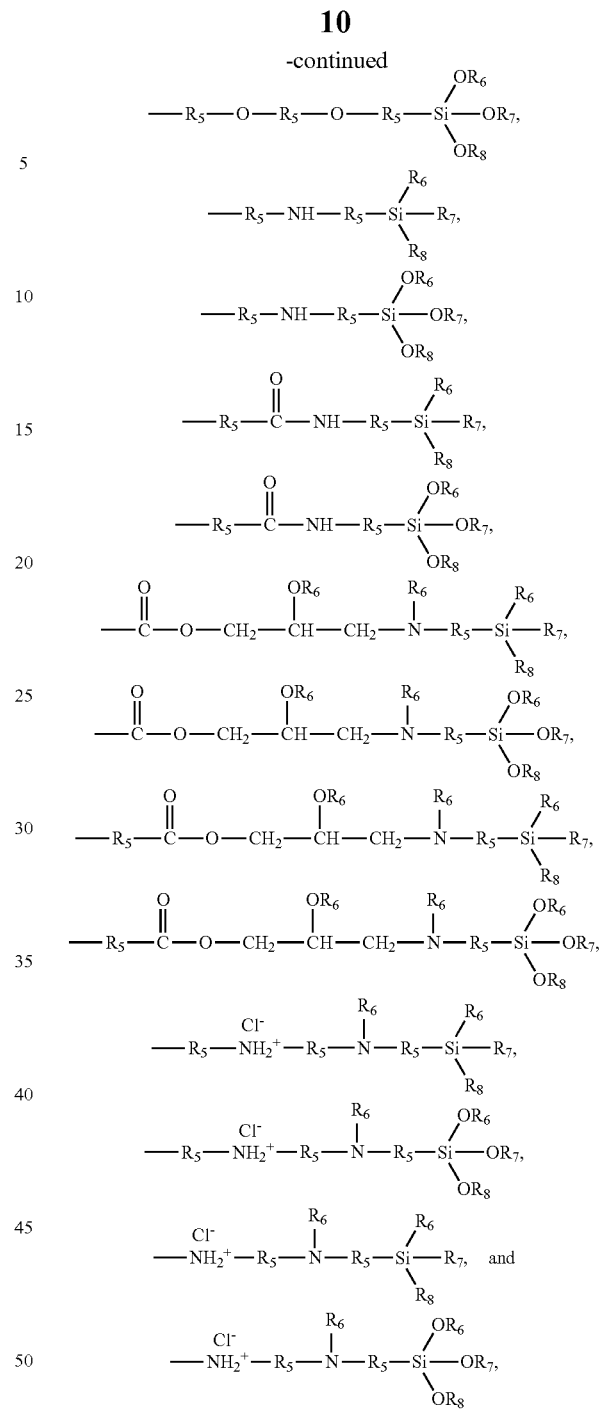

In the polar functional groups, independently, p is an integer from 1 to 10. R5 is substituted or unsubstituted linear or branched alkylene having 1 to 20 carbon atoms; substituted or unsubstituted linear or branched alkenylene having 2 to 20 carbon atoms; substituted or unsubstituted linear or branched alkynylene having 2 to 20 carbon atoms; substituted or unsubstituted cycloalkylene having 3 to 12 carbon atoms; substituted or unsubstituted arylene having 6 to 40 carbon atoms; substituted or unsubstituted carbonyloxylene having 1 to 20 carbon atoms; or substituted or unsubstituted alkoxylene having 1 to 20 carbon atoms. R6, R7 and R8 are independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted alkoxy having 1 to 20 carbon atoms; and substituted or unsubstituted carbonyloxy having 1 to 20 carbon atoms.

In the cyclic olefin compound, the substituted or unsubstituted aryl having 6 to 40 carbon atoms or the heteroaryl having 6 to 40 carbon atoms with an hetero element in Group 14, 15 or 16 is selected from the group consisting of the following functional groups; or may be other different aryl or heteroaryl groups:

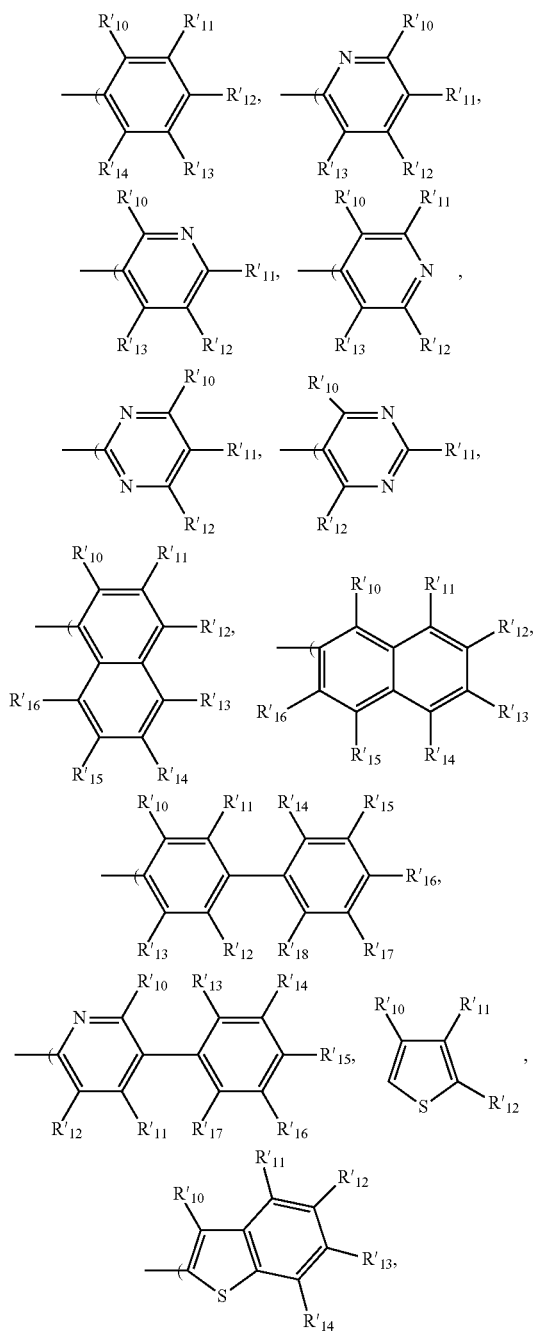

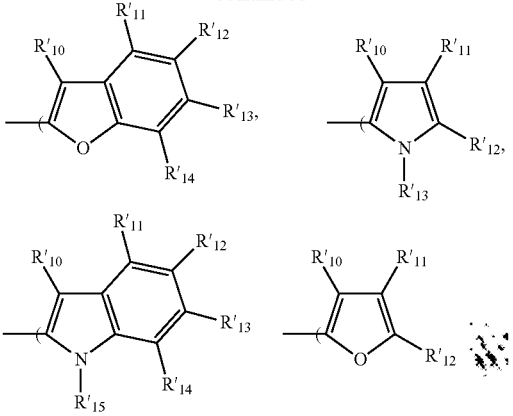

In the functional groups, R'10 to R'18 are the same as or different from one another and independently selected from the group consisting of substituted or unsubstituted linear or branched alkyl having 1 to 20 carbon atoms; substituted or unsubstituted alkoxy having 1 to 20 carbon atoms; substituted or unsubstituted aryloxy having 6 to 30 carbon atoms; and substituted or unsubstituted aryl having 6 to 40 carbon atoms.

In the cyclic olefin compound, at least one of the R1 to R4 of the formula 1 is a photoreactive group of the formula 1a or 1b. For example, at least one of R1 and R2 may be the photoreactive group. The use of the cyclic olefin compound enables the preparation of a photoreactive polymer having good characteristics such as alignment or the like.

In the above-described structure of the cyclic olefin compound, the respective substituents are defined as follows:

The term "alkyl" as used herein refers to a monovalent linear or branched saturated hydrocarbon portion having 1 to 20 carbon atoms, preferably 1 to 10 carbon atoms, more preferably 1 to 6 carbon atoms. The alkyl group inclusively refers to alkyl groups unsubstituted or additionally substituted with a specific substituent, which will be described later. The examples of the alkyl group may comprise methyl, ethyl, propyl, 2-propyl, n-butyl, iso-butyl, tert-butyl, pentyl, hexyl, dodecyl, fluoromethyl, difluoromethyl, trifluoromethyl, chloromethyl, dichloromethyl, trichloromethyl, iodomethyl, bromomethyl, etc.

The term "alkenyl" as used herein refers to a monovalent linear or branched hydrocarbon portion having 2 to 20 carbon atoms, preferably 2 to 10 carbon atoms, more preferably 2 to 6 carbon atoms with at least one carbon-carbon double bond. The alkenyl group may form a bonding through carbon atoms including a carbon-carbon double bond or through saturated carbon atoms. The alkenyl group inclusively refers to alkenyl groups unsubstituted or additionally substituted with a specific substituent, which will be described later. The examples of the alkenyl group may comprise ethenyl, 1-propenyl, 2-propenyl, 2-butenyl, 3-butenyl, pentenyl, 5-hexenyl, dodecenyl, etc.

The term "cycloalkyl" as used herein refers to a monovalent saturated or unsaturated mono-, bi- or tri-cyclic non-aromatic hydrocarbon portion having 3 to 12 ring-carbon atoms. The cycloalkyl group inclusively refers to cycloalkyl groups additionally substituted with a specific substituent, which will be described later. The examples of the cycloalkyl group may comprise cyclopropyl, cyclobutyl, cyclopentyl, cyclopentenyl, cyclohexyl, cyclohexenyl, cycloheptyl, cyclooctyl, decahydronaphthalenyl, adamantyl, norbornyl (i.e., bicyclo[2,2,1]hept-5-enyl), etc.

The term "aryl" as used herein refers to a monovalent mono-, bi- or tri-cyclic aromatic hydrocarbon portion having 6 to 40 ring-carbon atoms, preferably 6 to 12 ring-carbon atoms. The aryl group inclusively refers to aryl groups additionally substituted with a specific substituent, which will be described later. The examples of the aryl group may comprise phenyl, naphthalenyl, fluorenyl, etc.

The term "alkoxyaryl" as used herein refers to the above-defined aryl group in which at least one hydrogen atom is substituted by an alkoxy group. The examples of the alkoxyaryl group may comprise methoxyphenyl, ethoxyphenyl, propoxyphenyl, butoxyphenyl, pentoxyphenyl, hextoxyphenyl, heptoxy, octoxy, nanoxy, methoxybiphenyl, methoxynaphthalenyl, methoxyfluorenyl, methoxyanthracenyl, etc.

The term "aralkyl" as used herein refers to the above-defined alkyl group in which at least one hydrogen atom is substituted by an aryl group. The aralkyl group inclusively refers to aralkyl groups additionally substituted with a specific substituent, which will be described later. The examples of the aralkyl may comprise benzyl, benzhydryl, trityl, etc.

The term "alkynyl" as used herein refers to a monovalent linear or branched hydrocarbon portion having 2 to 20 carbon atoms, preferably 2 to 10 carbon atoms, more preferably 2 to 6 carbon atoms with at least one carbon-carbon triple bond. The alkynyl group may form a bonding through carbon atoms including a carbon-carbon triple bond or through saturated carbon atoms. The alkynyl group inclusively refers to alkynyl groups additionally substituted with a specific substituent, which will be described later. The examples of the alkynyl group may comprise ethynyl, propynyl, etc.

The term "alkylene" as used herein refers to a divalent linear or branched saturated hydrocarbon portion having 1 to 20 carbon atoms, preferably 1 to 10 carbon atoms, more preferably 1 to 6 carbon atoms. The alkylene group inclusively refers to alkylene groups additionally substituted with a specific substituent, which will be described later. The examples of the alkylene group may comprise methylene, ethylene, propylene, butylene, hexylene, etc.

The term "alkenylene" as used herein refers to a divalent linear or branched hydrocarbon portion having 2 to 20 carbon atoms, preferably 2 to 10 carbon atoms, more preferably 2 to 6 carbon atoms with at least one carbon-carbon double bond. The alkenylene group may form a bonding through carbon atoms including a carbon-carbon double bond and/or through saturated carbon atoms. The alkenylene group inclusively refers to alkenylene groups additionally substituted with a specific substituent, which will be described later.

The term "cycloalkylene" as used herein refers to a divalent saturated or unsaturated mono-, bi- or tri-cyclic non-aromatic hydrocarbon portion having 3 to 12 ring-carbon atoms. The cycloalkylene group inclusively refers to cycloalkylene groups additionally substituted with a specific substituent, which will be described later. The examples of the cycloalkylene group may comprise cyclopropylene, cyclobutylene, etc.

The term "arylene" as used herein refers to a divalent mono-, bi- or tri-cyclic aromatic hydrocarbon portion having 6 to 20 ring-carbon atoms, preferably 6 to 12 ring-carbon atoms. The arylene group inclusively refers to arylene groups additionally substituted with a specific substituent, which will be described later. The aromatic portion includes carbon atoms only. The examples of the arylene may comprise phenylene, etc.

The term "aralkylene" as used herein refers to a divalent portion of the above-defined alkyl group in which at least one hydrogen atom is substituted by an aryl group. The aralkylene group inclusively refers to aralkylene groups additionally substituted with a specific substituent, which will be described later. The examples of the aralkylene group may comprise benzylene, etc.

The term "alkynylene" as used herein refers to a divalent linear or branched hydrocarbon portion having 2 to 20 carbon atoms, preferably 2 to 10 carbon atoms, more preferably 2 to 6 carbon atoms with at least one carbon-carbon triple bond. The alkynylene group may form a bonding through carbon atoms including a carbon-carbon triple bond or through saturated carbon atoms. The alkynylene group inclusively refers to alkynylene groups additionally substituted with a specific substituent, which will be described later. The examples of the alkynylene group may comprise ethynylene, propynylene, etc.

In the above description, the phrase "a substituent is substituted or unsubstituted" has an inclusive meaning that the substituent is or isn't additionally substituted with the substituent itself or another specific substituent. If not stated otherwise in this specification, the examples of the substituent used as an additional substituent for each substituent may include halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, siloxy, or "a polar functional group comprising oxygen, nitrogen, phosphor, sulfur, silicon, or boron" as mentioned above.

The above-described cyclic olefin compound may be prepared by a typical method of introducing a defined substituent, more specifically, a photoreactive group of the formula 1a or 1b on a cyclic olefin such as a norbornene-based compound. The synthesis of the cyclic olefin compound involves, for example, a condensation reaction of norbornene (alkyl)ol, such as norbornene methanol, and a carboxylic compound or the like having a photoreactive group of the formula 1a or 1b. Depending on the structure and the type of the photoreactive group of the formula 1a or 1b, any other different methods can be used to introduce the photoreactive group and prepare the cyclic olefin compound.

In accordance with another embodiment of the invention, there is provided a photoreactive polymer comprising a repeating unit of the following formula 3a or 3b:

[Formula 3a]

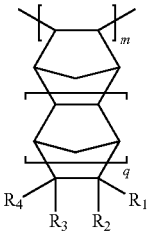

[Formula 3b]

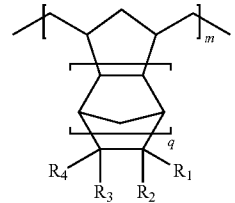

In the formulas 3a and 3b, independently, m is 50 to 5,000; and q, R1, R2, R3 and R4 are as defined in the formula 1.

This photoreactive polymer, which comprises a repeating unit derived from the cyclic olefin compound, supports the formation of a large free volume between adjacent photoreactive groups owing to the bulky aralkyl structure connected to the ends of the photoreactive groups via a linker L. In the photoreactive polymer, consequently, the photoreactive groups are relatively free to move (flow) or react in the secured large free volume. Hence, the photoreactive polymer can exhibit better excellences in photoreactivity, alignment rate, and photo-alignment. Further, the photoreactive polymer has the photoreactive groups relatively ready to change the alignment direction according to the polarization direction, thereby acquiring readiness for change in the alignment direction depending on the polarization direction and preferably being applied to patterned retarders, patterned cell alignment layers, or the like.

The photoreactive polymer may comprise a norbornene-based repeating unit of the formula 3a or 3b as a main repeating unit. The norbornene-based repeating unit is structurally rigid, and the photoreactive polymer comprising the norbornene-based repeating unit has a relatively high glass transition temperature Tg of about 300° C. or above, preferably about 300 to 350° C., consequently with a higher thermal stability than the existing photoreactive polymers.

The definitions of the respective substituents bonded to the photoreactive polymer are specified above in detail in regard to the cyclic olefin compound of the formula 1 and will not be described any more.

The photoreactive polymer may comprise at least one repeating unit selected from the group consisting of the repeating units of the formula 3a or 3b, or may be a copolymer further comprising another type of repeating unit. The examples of the repeating unit may comprise any olefin-, acrylate- or cyclic-olefin-based repeating unit with or without a bonding to cinnamate-, chalcone- or azo-based photoreactive groups. The exemplary repeating units are disclosed in Korean Patent Laid-open Publication No. 2010-0021751.

To prevent deterioration in good characteristics such as alignment and alignment rate pertaining to the formula 3a or 3b, the photoreactive polymer may comprise the repeating unit of the formula 3a or 3b in an amount of at least about 50 mol %, more specifically about 50 to 100 mol %, preferably at least about 70 mol %.

The repeating unit of the formula 3a or 3b constituting the photoreactive polymer has a degree of polymerization in the range of about 50 to 5,000, preferably about 100 to 4,000, more preferably about 1,000 to 3,000. The photoreactive polymer has a weight average molecular weight of 10,000 to 1000,000, preferably 20,000 to 500,000. The photoreactive polymer properly included in a coating composition for forming an alignment layer provides the coating composition with good coatability and the alignment layer formed from the coating composition with good liquid crystal alignment.

The photoreactive polymer may be endowed with photoreactivity upon exposure to a polarized radiation having a wavelength of about 150 to 450 nm. For example, the photoreactive polymer can exhibit excellences in photoreactivity and alignment upon exposure to polarized UV radiation having a wavelength of about 200 to 400 nm, more specifically about 250 to 350 nm.

In accordance with still another embodiment of the invention, there is provided a method for preparing the photoreactive polymer. An example of the preparation method comprises performing an addition polymerization reaction using a monomer represented by the formula 1 in the presence of a catalyst composition comprising a precatalyst containing a transition metal in Group 10, and a cocatalyst:

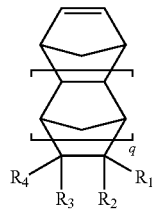

[Formula 1]

In the formula 1, q, R1, R2, R3 and R4 are as defined in the formula 3a.

The polymerization reaction may be carried out at a temperature of 10 to 200° C. The polymerization temperature below 10° C. lowers the polymerization activity, while the temperature above 200° C. undesirably causes a cleavage of the catalyst.

The cocatalyst comprises at least one selected from the group consisting of a first cocatalyst providing a Lewis base capable of forming a weak coordinate bond with the metal of the precatalyst; and a second cocatalyst providing a compound comprising a Group 15 electron donor ligand. Preferably, the cocatalyst may be a catalyst mixture comprising the first cocatalyst providing a Lewis base, and optionally the second cocatalyst providing a compound comprising a neutral Group 15 electron donor ligand.

The catalyst mixture may comprise, based on one mole of the precatalyst, 1 to 1,000 moles of the first cocatalyst and 1 to 1,000 moles of the second cocatalyst. The excessively low content of the first or second cocatalyst causes a failure to provide the catalyst activity enough, while an excess of the first or second cocatalyst deteriorates the catalyst activity.

The precatalyst comprising a Group 10 transition metal may be a compound having a Lewis base functional group that is readily leaving from the central transition metal by the first cocatalyst providing a Lewis base and participating in a Lewis acid-base reaction to help the central transition metal change into a catalyst active species. The examples of the precatalyst include allylpalladium chloride dimer ([(Allyl)Pd(Cl)]$_2$), palladium(II) acetate ((CH$_3$CO$_2$)$_2$Pd), palladium(II) acetylacetonate ([CH$_3$COCH=C(O—)CH$_3$]$_2$Pd), NiBr(NP(CH$_3$)$_3$)$_4$, [PdCl(NB)O(CH$_3$)]$_2$, etc.

The first cocatalyst providing a Lewis base capable of forming a weak coordinate bond with the metal of the precatalyst may be a compound that readily reacts with a Lewis base to leave vacancies in the transition metal and forms a weak coordinate bond with a transition metal compound in order to stabilize the resultant transition metal; or a compound providing such a compound. The examples of the first cocatalyst may include borane (e.g., B(C$_6$F$_5$)$_3$), borate (e.g., dimethylanilinium tetrakis(pentafluorophenyl)borate), alkylaluminum (e.g., methylaluminoxane (MAO) or Al(C$_2$H$_5$)$_3$), transition metal halide (e.g., AgSbF$_6$), etc.

The examples of the second cocatalyst that provides a compound comprising a neutral Group 15 electron donor ligand may include alkyl phosphine, cycloalkyl phosphine, or phenyl phosphine.

The first and second cocatalysts may be used separately, or used together to form a single salt compound used as a compound for activating the catalyst. For example, there may be a compound prepared as an ion pair of alkyl phosphine and a borane or borate compound.

The above-described method may be used to prepare a repeating unit of the formula 3a and a photoreactive polymer according to an embodiment comprising the repeating unit.

As for a photoreactive polymer further comprising an olefin-, cyclic-olefin- or acrylate-based repeating unit, typical preparation methods are used for forming each of the corresponding repeating units, which is then copolymerized with the repeating unit of the formula 3a prepared by the above-described method to form the photoreactive polymer.

On the other hand, a photoreactive polymer comprising a repeating unit of the formula 2a may be prepared according to another example of the preparation method. The another exemplary preparation method comprises performing a ring-opening polymerization using a monomer of the formula 1 in the presence of a catalyst composition comprising a precatalyst containing a transition metal in Group 4, 6 or 8, and a cocatalyst to form a repeating unit of the formula 3b. Alternatively, the photoreactive polymer comprising a repeating unit of the formula 3b may be prepared by a method that comprises performing a ring-opening polymerization using norbornene (alkyl)ol, such as norbornene methanol, as a norbornene monomer in the presence of a catalyst composition comprising a precatalyst containing a transition metal in Group 4, 6 or 8, and a cocatalyst to form a ring-opened polymer with a 5-membered ring, and then introducing a photoreactive group on the ring-opened polymer to complete the photoreactive polymer. Here, the introduction of the photoreactive group may be achieved using a condensation reaction of the ring-opened polymer with a carboxylate compound or an acyl chloride compound having a photoreactive group of the formula 1a or 1b.

The ring-opening polymerization step may involve hydrogenation of the double bond of the norbornene ring included in the monomer of the formula 1 to open the norbornene ring, simultaneously beginning a polymerization reaction to prepare a repeating unit of the formula 3b and a photoreactive polymer comprising the repeating unit. Alternatively, polymerization and ring-opening reactions may occur in sequence to form the photoreactive polymer.

The ring-opening polymerization may be carried out in the presence of a catalyst composition, which comprises a precatalyst containing a transition metal in Group 4 (e.g., Ti, Zr, or Hf), Group 6 (e.g., Mo, or W) or Group 8 (e.g., Ru, or Os); a cocatalyst providing a Lewis base capable of forming a weak coordinate bond with the metal of the precatalyst; and optionally a neutral Group 15 or 16 activator for improving the activity of the metal in the precatalyst. In the presence of the catalyst composition, a linear alkene, such as 1-alkene, 2-alkene, etc., controllable in molecular weight is added in an amount of 1 to 100 mol % with respect to the monomer to catalyze a polymerization reaction at 10 to 200° C. Then, a catalyst comprising a transition metal in Group 4 (e.g., Ti, or Zr) or Groups 8 to 10 (e.g., Ru, Ni, or Pd) is added in an amount of 1 to 30 wt. % with respect to the monomer to catalyze a hydrogenation reaction on the double bond of the norbornene ring at 10 to 250° C.

The excessively lower reaction temperature deteriorates the polymerization activity, and the excessively higher reaction temperature results in an undesirable cleavage of the catalyst. The lower hydrogenation temperature deteriorates the reaction activity, while the excessively high hydrogenation temperature causes a cleavage of the catalyst.

The catalyst composition comprises one mole of a precatalyst containing a transition metal in Group 4 (e.g., Ti, Zr, or Hf), Group 6 (e.g., Mo, or W) or Group 8 (e.g., Ru, or Os); 1 to 100,000 moles of a cocatalyst providing a Lewis base capable of forming a weak coordinate bond with the metal of the precatalyst; and optionally 1 to 100 moles of an activator comprising a neutral Group 15 or 16 element for improving the activity of the metal of the precatalyst.

The cocatalyst content less than one mole causes a failure in activation of the catalyst, and the cocatalyst content greater than 100,000 moles deteriorates the catalyst activity. The activator may be unnecessary depending on the type of the precatalyst. The activator content less than one mole ends up with a failure of the catalyst activation, while the activator content greater than 100 moles results in a lower molecular weight.

The hydrogenation reaction fails to occur when the content of the catalyst comprising a transition metal of Group 4 (e.g., Ti, or Zr) or Group 8, 9 or 10 (e.g., Ru, Ni, or Pd) for hydrogenation reaction is less than 1 wt. % with respect to the monomer. The catalyst content greater than 30 wt. % undesirably results in a discoloration of the polymer.

The precatalyst comprising a transition metal in Group 4 (e.g., Ti, Zr, or Hf), Group 6 (e.g., Mo, or W) or Group 8 (e.g., Ru, or Os) may refer to a transition metal compound, such as $TiCl_4$, $WCl_6$, $MoCl_5$, $RuCl_3$, or $ZrCl_4$, having a functional group that is readily leaving from the central transition metal by the first cocatalyst providing a Lewis base and participating in a Lewis acid-base reaction to help the central transition metal change into a catalyst active species.

The examples of the cocatalyst providing a Lewis base capable of forming a weak coordinate bond with the metal of the precatalyst may include borane, such as $B((C_6F_5)_3$, or borate; or alkylaluminum, alkylaluminum halide or aluminum halide, such as methylaluminoxane (MAO), $Al(C_2H_5)_3$, or $Al(CH_3)Cl_2$. Here, aluminum may be replaced by a substituent, such as lithium, magnesium, germanium, lead, zinc, tin, silicon, etc. Hence, the cocatalyst is a compound that readily reacts with a Lewis base to provide vacancies in the transition metal and forms a weak coordinate bond with the transition metal compound in order to stabilize the produced transition metal; or a compound providing such a compound.

Depending on the type of the precatalyst, a polymerization activator is required or not. The examples of the activator comprising a neutral element in Group 15 or 16 may include water, methanol, ethanol, isopropyl alcohol, benzylalcohol, phenol, ethyl mercaptan, 2-chloroethanol, trimethylamine, triethylamine, pyridine, ethylene oxide, benzoyl peroxide, t-butyl peroxide, or the like.

The catalyst comprising a transition metal in Group 4 (e.g., Ti, or Zr) or Group 8, 9 or 10 (e.g., Ru, Ni, or Pd) used for hydrogenation reaction may be prepared as a homogeneous form miscible with a solvent, or as a metal complex catalyst impregnated on a particulate support. Preferably, the examples of the particulate support include silica, titania, silica/chromia, silica/chromia/titania, silica/alumina, aluminum phosphate gel, silanized silica, silica hydrogel, montmorillonite clay, or zeolite.

The above-described method is used to prepare the repeating unit of the formula 3b and the photoreactive polymer of the embodiment comprising the repeating unit. As for the photoreactive polymer that further comprises an olefin-, cyclic-olefin- or acrylate-based repeating unit, the respective repeating units are first formed through the corresponding preparation methods and then copolymerized with a repeating unit of the formula 3b prepared by the above-described method to form the photoreactive polymer.

In accordance with still another embodiment of the invention, there is provided an alignment layer comprising the above-described photoreactive polymer. The alignment layer may be of a thin film form or an alignment layer form. In accordance with further another embodiment of the invention, there is provided a liquid crystal retardation film comprising the alignment layer, and a liquid crystal layer on the alignment layer.

The alignment layer and the liquid crystal retardation film may be prepared using known preparation methods with constituent components known to those skilled in the art, excepting that a photo-aligned polymer is used as the photoreactive polymer.

For example, the alignment layer is prepared by mixing the photoreactive polymer with a binder resin and a photo-initiator, dissolving the mixture in an organic solvent to obtain a coating composition, applying the coating composition on a base, and then curing the coating composition by UV exposure.

Here, the binder resin may be an acrylate-based resin, more specifically, pentaerythritol triarylate, dipentaerythritol hexaacrylate, trimethylolpropane triacrylate, tris(2-acryloyloxyethyl) isocyanurate, etc.

The photo-initiator may be any typical photo-initiator known to be applicable to alignment layers without any limitations, such as, for example, Irgacure 907 or Irgacure 819.

The examples of the organic solvent may include toluene, anisole, chlorobenzene, dichloroethane, cyclohexane, cyclopentane, propylene glycol, methyl ether, acetate, etc. Other organic solvent may also be used without any limitations, because the photoreactive norbornene-based copolymer has a good solubility in various organic solvents.

In the coating composition, the content of the solid components comprising the binder resin and the photo-initiator may be in the range of 1 to 15 wt. %, preferably 10 to 15 wt. % to cast the alignment layer into films, or 1 to 5 wt. % to cast the alignment layer into thin films.

The alignment layer may be formed, for example, on a support as shown in FIG. 1, or under liquid crystals to achieve liquid crystal alignment. Here, the base may be a cyclic polymer base, an acryl polymer base, or a cellulose polymer base. The coating composition is applied on the base by different methods, such as bar coating, spin coating, blade coating, etc. and then cured under UV exposure to form an alignment layer.

The UV curing causes photo-alignment, in which step a polarized UV radiation having a wavelength of about 150 to 450 nm is applied to bring about alignment. Here, the exposure intensity of the radiation is about 50 mJ/cm$^2$ to 10 J/cm$^2$, preferably, about 500 mJ/cm$^2$ to 5 J/c m$^2$.

The UV radiation as used herein may be any UV radiations polarized by passing through or being reflected from (a) a polarizer using a dielectric anisotropic coating on the surface of a transparent substrate such as quartz glass, soda-lime glass, soda-lime-free glass, or the like; (b) a polarizer with fine aluminum or other metallic wires; or (c) a Brewster polarizer using reflection from quartz glass.

The substrate temperature during UV exposure is preferably the room temperature. Under circumstances, the substrate may be heated at 100° C. or below during UV exposure. Preferably, the final layer thus obtained from the above-described steps has a thickness of about 30 to 1,000 μm.

The above-described method is adopted to form an alignment layer and a liquid crystal layer on the alignment layer, completing a liquid crystal retardation film according to a typical method. The use of the photoreactive polymer in the alignment layer enables the alignment layer to have good interactions with liquid crystal molecules, achieving effective photo-alignment.

The alignment layer or the liquid crystal retardation film is applicable to optical films or filters used to create stereoscopic images.

In accordance with still further another embodiment of the invention, there is provided a display device comprising the alignment layer. The display device may be a liquid crystal display device comprising the alignment layer for liquid crystal alignment; or a stereoscopic imaging display device included in optical films or filters to create stereoscopic images. The constituent components of the display device are the same as those of a typical display device, excepting that the photoreactive polymer and the alignment layer are included, and will not be described any more in further detail.

In the following are set forth preferred examples of the invention for better understanding of the invention. It is to be understood that the examples are only for illustrative purposes and are not intended to limit the scope of the invention.

EXAMPLE 1

Preparation of 4-benzyloxy-cinnamate-5-norbornene (Cyclic Olefin Compound)

4-Benzyloy-benzaldehyde (10 g, 47 mmol), malonic acid (2 eq.) and piperidine (0.1 eq.) were dissolved in pyridine (5 eq.) and stirred at 80° C. for 5 hours. After completion of the reaction, the reaction mixture was cooled down to the room temperature and neutralized with 3M HCl. The white solid thus obtained was filtered out and dried in a vacuum oven to yield 4-benzyloxy-cinnamic acid.

The 4-benzyloxy-cinnamic acid (5 g, 19.7 mmol), norbornene-5-ol (19 mmol) and Zr(AcAc) (0.2 mol. %) were put in xylene and stirred at 190° C. for 24 hours. Then, the reaction mixture was washed with 1M HCl and 1M NaHCO3 aqueous solutions and removed of the solvent to obtain a yellowish solid, 4-benzyloxy-cinnamate-5-norbornene.

NMR(CDCl$_3$ (500 MHz), ppm): 0.6(1, m) 1.22~1.27(2, m) 1.47(1, d) 1.87(1, m) 2.56(1, m) 2.93(1, s) 5.11(2, s) 5.98~6.19(2, m) 6.36(1, d) 7.3~7.5(9, m) 7.63(2, d).

EXAMPLE 2

Preparation of 4-benzyloxy-cinnamate-5-methyl norbornene (Cyclic Olefin Compound)

The procedures were performed in the same manner as described in Example 1, excepting that norbornene-5-methanol was used instead of norbornene-5-ol to prepare 4-benzyloxy-cinnamate-5-methyl norbornene.

NMR(CDCl$_3$ (500 MHz), ppm): 0.6(1, m) 1.22~1.27 (2, m) 1.47(1,d) 1.87(1, m) 2.47(1, m) 2.93(1, s) 3.8~4.25(2, m) 5.11(2, s) 5.98~6.19(2, m) 6.36(1,d) 7.3~7.5(9, m) 7.63(2, d).

EXAMPLE 3

Preparation of 4-benzyloxy-cinnamate-5-ethyl norbornene (Cyclic Olefin Compound)

The procedures were performed in the same manner as described in Example 1, excepting that norbornene-5-ethanol was used instead of norbornene-5-ol to prepare 4-benzyloxy-cinnamate-5-ethyl norbornene.

NMR(CDCl$_3$ (500 MHz), ppm): 0.6(1, m) 1.22~1.27(2, m) 1.33~1.6(3, m) 1.8(1, m) 2.43(1, m) 2.90(1, s) 3.3~3.9(2, m) 5.11(2, s) 5.95~6.17(2, m) 6.36(1,d) 7.3~7.5(9, m) 7.63(2, d).

EXAMPLE 4

Preparation of 4-(4-fluoro-benzyloxy)-cinnamate-5-norbornene (Cyclic Olefin Compound)

The procedures were performed in the same manner as described in Example 1, excepting that 4-(4-fluoro-benzyloxy)-benzaldehyde was used instead of 4-benzyloxy-benzaldehyde to prepare 4-(4-fluoro-benzyloxy)-cinnamate-5-norbornene.

NMR(CDCl₃ (500 MHz), ppm): 0.6(1, m) 1.22~1.27(2, m) 1.47(1,d) 1.88(1, m) 2.67(1, m) 2.93(1, s) 5.05(2, s) 5.97~6.11(2, m) 6.30(1,d) 6.97(2, d) 7.1(2, m) 7.4(2, m) 7.49(2, d) 7.65(1, s).

EXAMPLE 5

Preparation of
4-(4-fluoro-benzyloxy)-cinnamate-5-methyl
norbornene (Cyclic Olefin Compound)

The procedures were performed in the same manner as described in Example 4, excepting that norbornene-5-methanol was used instead of norbornene-5-ol to prepare 4-(4-fluoro-benzyloxy)-cinnamate-5-methyl norbornene.

NMR(CDCl₃ (500 MHz), ppm): 0.6(1, m) 1.22~1.27(2, m) 1.47(1,d) 1.88(1, m) 2.47(1, m) 2.93(1, s) 5.05(2, s) 5.97~6.11(2, m) 6.30(1,d) 6.97(2, d) 7.1(2, m) 7.4(2, m) 7.49(2, d) 7.65(1, s).

EXAMPLE 6

Preparation of
4-(4-fluoro-benzyloxy)-cinnamate-5-ethyl
norbornene (Cyclic Olefin Compound)

The procedures were performed in the same manner as described in Example 4, excepting that norbornene-5-ethanol was used instead of norbornene-5-ol to prepare 4-(4-fluoro-benzyloxy)-cinnamate-5-ethyl norbornene.

NMR(CDCl₃ (500 MHz), ppm): 0.6(1, m) 1.22~1.27(2, m) 1.36~1.6(3, m) 1.86(1, m) 2.45(1, m) 2.91(1, s) 3.32~3.96(2, m) 5.05(2, s) 5.97~6.11(2, m) 6.30(1, d) 6.97(2, d) 7.1(2, m) 7.4(2, m) 7.49(2, d) 7.65(1, s).

EXAMPLE 7

Preparation of
4-(4-methyl-benzyloxy)-cinnamate-5-norbornene
(Cyclic Olefin Compound)

The procedures were performed in the same manner as described in Example 1, excepting that 4-(4-methyl-benzyloxy)-benzaldehyde was used instead of 4-benzyloxy-benzaldehyde to prepare 4-(4-methyl-benzyloxy)-cinnamate-5-norbornene.

NMR(CDCl₃ (500 MHz), ppm): 0.6(1, m) 1.21~1.27(2, m) 1.47(1,d) 1.88(1, m) 2.37(3, s) 2.67(1, m) 2.93(1, s) 5.05(2, s) 5.97~6.11(2, m) 6.30(1, d) 6.97(2, m) 7.1(2, m) 7.4(2, m) 7.45(2, d) 7.65(1, s).

EXAMPLE 8

Preparation of
4-(4-methyl-benzyloxy)-cinnamate-5-methyl
norbornene (Cyclic Olefin Compound)

The procedures were performed in the same manner as described in Example 7, excepting that norbornene-5-methanol was used instead of norbornene-5-ol to prepare 4-(4-methyl-benzyloxy)-cinnamate-5-methyl norbornene.

NMR(CDCl₃ (500 MHz), ppm): 0.6(1, m) 1.22~1.27(2, m) 1.47(1,d) 1.88(1, m) 2.37(3, s) 2.47(1, m) 2.93(1, s) 3.74~4.28(2, m) 5.05(2, s) 5.97~6.11(2, m) 6.30(1, d) 6.97(2, d) 7.1(2, m) 7.4(2, m) 7.47(2, d) 7.65(1, s).

EXAMPLE 9

Preparation of
4-(4-methyl-benzyloxy)-cinnamate-5-ethyl
norbornene (Cyclic Olefin Compound)

The procedures were performed in the same manner as described in Example 7, excepting that norbornene-5-ethanol was used instead of norbornene-5-ol to prepare 4-(4-methyl-benzyloxy)-cinnamate-5-ethyl norbornene.

NMR(CDCl₃ (500 MHz), ppm): 0.6(1, m) 1.22~1.27(2, m) 1.35~1.6(3, m) 1.86(1, m) 2.37(3, s) 2.45(1, m) 2.91(1, s) 3.33~3.96(2, m) 5.05(2, s) 5.97~6.11(2, m) 6.30(1, d) 6.97(2, d) 7.1(2, m) 7.4(2, m) 7.49(2, d) 7.65(1, s).

EXAMPLE 10

Preparation of
4-(4-methoxy-benzyloxy)-cinnamate-5-norbornene
(Cyclic Olefin Compound)

The procedures were performed in the same manner as described in Example 1, excepting that 4-(4-methoxy-benzyloxy)-benzaldehyde was used instead of 4-benzyloxy-benzaldehyde to prepare 4-(4-methoxy-benzyloxy)-cinnamate-5-norbornene.

NMR(CDCl₃ (500 MHz), ppm): 0.6(1, m) 1.20~1.27(2, m) 1.47(1,d) 1.88(1, m) 2.67(1, m) 2.93(1, s) 4.44(3, s) 5.05(2, s) 5.98~6.11(2, m) 6.30(1, d) 7.01(2, d) 7.16(2, m) 7.44(2, m) 7.51(2, d) 7.65(1, s).

EXAMPLE 11

Preparation of
4-(4-methoxy-benzyloxy)-cinnamate-5-methyl
norbornene (Cyclic Olefin Compound)

The procedures were performed in the same manner as described in Example 10, excepting that norbornene-5-methanol was used instead of norbornene-5-ol to prepare 4-(4-methoxy-benzyloxy)-cinnamate-5-methyl norbornene.

NMR(CDCl₃ (500 MHz), ppm): 0.6(1, m) 1.22~1.27(2, m) 1.47(1,d) 1.88(1, m) 2.47(1, m) 2.93(1, s) 3.75~4.3(2, m) 5.05(2, s) 5.97~6.11(2, m) 6.30(1, d) 6.97(2, d) 7.01(2, d) 7.16(2, m) 7.44(2, m) 7.51(2, d) 7.65(1, s).

EXAMPLE 12

Preparation of
4-(4-methoxy-benzyloxy)-cinnamate-5-ethyl
norbornene (Cyclic Olefin Compound)

The procedures were performed in the same manner as described in Example 10, excepting that norbornene-5-ethanol was used instead of norbornene-5-ol to prepare 4-(4-methoxy-benzyloxy)-cinnamate-5-ethyl norbornene.

NMR(CDCl₃ (500 MHz), ppm): 0.6(1, m) 1.22~1.27(2, m) 1.33~1.57(3, m) 1.86(1, m) 2.45(1, m) 2.92(1, s) 3.32~3.96

(2, m) 5.05(2, s) 5.97~6.11(2, m) 6.30(1, d) 7.01(2, d) 7.16(2, m) 7.44(2, m) 7.51(2, d) 7.65(1, s).

EXAMPLE 13

Preparation of 4-(2-naphthalene-methyloxy)-cinnamate-5-norbornene (Cyclic Olefin Compound)

The procedures were performed in the same manner as described in Example 1, excepting that 4-(2-naphthalene-methyloxy)-benzaldehyde was used instead of 4-benzyloxy-benzaldehyde to prepare 4-(2-naphthalene-methyloxy)-cinnamate-5-norbornene.

NMR(CDCl$_3$ (500 MHz), ppm): 0.6(1, m) 1.22~1.27(2, m) 1.47(1,d) 1.88(1, m) 2.64(1, m) 2.93(1, s) 5.28(2, s) 5.97~6.11(2, m) 6.31(1, d) 6.63(2, d) 7.5(6, m) 7.9(4, m).

EXAMPLE 14

Preparation of 4-(2-naphthalene-methyloxy)-cinnamate-5-methyl norbornene (Cyclic Olefin Compound)

The procedures were performed in the same manner as described in Example 13, excepting that norbornene-5-methanol was used instead of norbornene-5-ol to prepare 4-(2-naphthalene-methyloxy)-cinnamate-5-methyl norbornene.

NMR(CDCl$_3$ (500 MHz), ppm): 0.6(1, m) 1.22~1.27(2, m) 1.47(1,d) 1.88(1, m) 2.48(1, m) 2.91(1, s) 3.75~4.3(2, m) 5.28(2, s) 5.97~6.11(2, m) 6.31(1, d) 6.63(2, d) 7.5(6, m) 7.9(4, m).

EXAMPLE 15

Preparation of 4-(2-naphthalene-methyloxy)-cinnamate-5-ethyl norbornene (Cyclic Olefin Compound)

The procedures were performed in the same manner as described in Example 13, excepting that norbornene-5-ethanol was used instead of norbornene-5-ol to prepare 4-(2-naphthalene-methyloxy)-cinnamate-5-ethyl norbornene.

NMR(CDCl$_3$ (500 MHz), ppm): 0.6(1, m) 1.21~1.27(2, m) 1.37~1.6(3, m) 1.86(1, m) 2.45(1, m) 2.90(1, s) 3.62~4.05(2, m) 5.05(2, s) 5.97~6.11(2, m) 6.31(1, d) 6.63(2, d) 7.5(6, m) 7.9(4, m).

EXAMPLE 16

Preparation of 4-(4-methylketone benzyloxy)-cinnamate-5-norbornene (Cyclic Olefin Compound)

The procedures were performed in the same manner as described in Example 1, excepting that 4-(4-methylketone benzyloxy)-benzaldehyde was used instead of 4-benzyloxy-benzaldehyde to prepare 4-(4-methylketone benzyloxy)-cinnamate-5-norbornene.

NMR(CDCl$_3$ (500 MHz), ppm): 0.6(1, m) 1.22~1.27(2, m) 1.47(1,d) 1.88(1, m) 2.67(1, m) 2.93(1, s) 3.66(3, s) 5.05(2, s) 5.97~6.11(2, m) 6.27(1, d) 7.0(2, d) 7.1(2, m) 7.4(2, m) 7.50(2, d) 7.65(1, s).

EXAMPLE 17

Preparation of 4-(4-methylketone benzyloxy)-cinnamate-5-methyl norbornene (Cyclic Olefin Compound)

The procedures were performed in the same manner as described in Example 16, excepting that norbornene-5-methanol was used instead of norbornene-5-ol to prepare 4-(4-methylketone benzyloxy)-cinnamate-5-methyl norbornene.

NMR(CDCl$_3$ (500 MHz), ppm): 0.6(1, m) 1.22~1.27(2, m) 1.47(1,d) 1.87(1, m) 2.47(1, m) 2.93(1, s) 3.66(3, s) 3.8~4.25 (2, m) 5.05(2, s) 5.97~6.11(2, m) 6.27(1, d) 7.0(2, d) 7.1(2, m) 7.4(2, m) 7.50(2, d) 7.65(1, s).

EXAMPLE 18

Preparation of 4-(4-methylketone benzyloxy)-cinnamate-5-ethyl norbornene (Cyclic Olefin Compound)

The procedures were performed in the same manner as described in Example 16, excepting that norbornene-5-ethanol was used instead of norbornene-5-ol to prepare 4-(4-methylketone benzyloxy)-cinnamate-5-ethyl norbornene.

NMR(CDCl$_3$ (500 MHz), ppm): 0.6(1, m) 1.24~1.29(2, m) 1.33~1.6(3, m) 1.8(1, m) 2.43(1, m) 2.90(1, s) 3.66(3, s) 3.8~4.25(2, m) 5.05(2, s) 5.97~6.11(2, m) 6.27(1, d) 7.0(2, d) 7.1(2, m) 7.4(2, m) 7.50(2, d) 7.65(1, s).

EXAMPLE 19

Preparation of 4-(1-phenyl perfluoroheptyloxy)-cinnamate-5-norbornene (Cyclic Olefin Compound)

The procedures were performed in the same manner as described in Example 1, excepting that 4-(1-phenyl perfluoroheptyloxy)-benzaldehyde was used instead of 4-benzyloxy-benzaldehyde to prepare 4-(1-phenyl perfluoroheptyloxy)-cinnamate-5-norbornene.

NMR (CDCl$_3$ (500 MHz), ppm): 0.6 (1, m) 1.22~1.27(2, m) 1.47(1,d) 1.87(1, m) 2.56(1, m) 2.93(1, s) 5.10(2, s) 5.96~6.16(2, m) 6.55(1, d) 7.4~7.55(5, m) 7.65(2, d) 7.68(4, m).

EXAMPLE 20

Preparation of 4-(1-phenyl perfluoroheptyloxy)-cinnamate-5-methyl norbornene (Cyclic Olefin Compound)

The procedures were performed in the same manner as described in Example 19, excepting that norbornene-5-methanol was used instead of norbornene-5-ol to prepare 4-(1-phenyl perfluoroheptyloxy)-cinnamate-5-methyl norbornene.

NMR(CDCl$_3$ (500 MHz), ppm): 0.6(1, m) 1.22~1.27(2, m) 1.47(1,d) 1.87(1, m) 2.56(1, m) 2.93(1, s) 3.75~4.3(2, m) 5.10(2, s) 5.96~6.16(2, m) 6.55(1, d) 7.4~7.55(5, m) 7.65(2, d) 7.68(4, m).

EXAMPLE 21

Preparation of 4-(1-phenyl perfluoroheptyloxy)-cinnamate-5-ethyl norbornene (Cyclic Olefin Compound)

The procedures were performed in the same manner as described in Example 19, excepting that norbornene-5-ethanol was used instead of norbornene-5-ol to prepare 4-(1-phenyl perfluoroheptyloxy)-cinnamate-5-ethyl norbornene.

NMR(CDCl$_3$ (500 MHz), ppm): 0.6(1, m) 1.22~1.27(2, m) 1.34~1.59(3, m) 1.86(1, m) 2.56(1, m) 2.92(1, s) 3.31~3.96 (2, m) 5.10(2, s) 5.96~6.16(2, m) 6.55(1, d) 7.4~7.55(5, m) 7.65(2, d) 7.68(4, m).

EXAMPLE 22

Preparation of 4-(4-benzyloxy)-benzyloxy-cinnamate-5-norbornene (Cyclic Olefin Compound)

The procedures were performed in the same manner as described in Example 1, excepting that 4-(4-benzyloxy)-benzyloxy-benzaldehyde was used instead of 4-benzyloxy-benzaldehyde to prepare 4-(4-benzyloxy)-benzyloxy-cinnamate-5-norbornene.

NMR(CDCl$_3$ (500 MHz), ppm): 0.6(1, m) 1.22~1.27(2, m) 1.47(1,d) 1.88(1, m) 2.67(1, m) 2.93(1, s) 5.16(4, s) 5.97~6.11(2, m) 6.30(1, d) 6.99~7.15(8,d) 7.4~7.51(5, d) 7.61(1, s).

EXAMPLE 23

Preparation of 4-(4-benzyloxy)-benzyloxy-cinnamate-5-methyl norbornene (Cyclic Olefin Compound)

The procedures were performed in the same manner as described in Example 22, excepting that norbornene-5-methanol was used instead of norbornene-5-ol to prepare 4-(4-benzyloxy)-benzyloxy-cinnamate-5-methyl norbornene.

NMR(CDCl$_3$ (500 MHz), ppm): 0.6(1, m) 1.22~1.27(2, m) 1.47(1,d) 1.88(1, m) 2.47(1, m) 2.93(1, s) 3.75~4.3(2, m) 5.16(4, s) 5.97~6.11(2, m) 6.30(1, d) 6.99~7.15(8,d) 7.4~7.51(5, d) 7.61(1, s).

EXAMPLE 24

Preparation of 4-(4-benzyloxy)-benzyloxy-cinnamate-5-ethyl norbornene (Cyclic Olefin Compound)

The procedures were performed in the same manner as described in Example 22, excepting that norbornene-5-ethanol was used instead of norbornene-5-ol to prepare 4-(4-benzyloxy)-benzyloxy-cinnamate-5-ethyl norbornene.

NMR(CDCl$_3$ (500 MHz), ppm): 0.6(1, m) 1.22~1.27(2, m) 1.36~1.6(3, m) 1.86(1, m) 2.45(1, m) 2.91(1, s) 3.32~3.96(2, m) 5.16(4, s) 5.97~6.11(2, m) 6.30(1, d) 6.99~7.15(8,d) 7.4~7.51(5, d) 7.61(1, s).

EXAMPLE 25

Preparation of 4-(4-fluoro-phenyloxy)-benzyloxy-cinnamate-5-norbornene (Cyclic Olefin Compound)

The procedures were performed in the same manner as described in Example 1, excepting that 4-(4-fluoro-phenyloxy)-benzyloxy-benzaldehyde was used instead of 4-benzyloxy-benzaldehyde to prepare 4-(4-fluoro-phenyloxy)-benzyloxy-cinnamate-5-norbornene.

NMR(CDCl$_3$ (500 MHz), ppm): 0.6(1, m) 1.22~1.27(2, m) 1.47(1,d) 1.88(1, m) 2.55(1, m) 2.91(1, s) 5.08(4, s) 5.91~6.11(2, m) 6.30(1, d) 6.97(2,d) 7.20(2, m) 7.31~7.63(8, m) 7.68(1, s) 7.84(2, d).

EXAMPLE 26

Preparation of 4-(4-fluoro-phenyloxy)-benzyloxy-cinnamate-5-methyl norbornene (Cyclic Olefin Compound)

The procedures were performed in the same manner as described in Example 25, excepting that norbornene-5-methanol was used instead of norbornene-5-ol to prepare 4-(4-fluoro-phenyloxy)-benzyloxy-cinnamate-5-methyl norbornene.

NMR(CDCl$_3$ (500 MHz), ppm): 0.6(1, m) 1.22~1.27(2, m) 1.47(1,d) 1.88(1, m) 2.55(1, m) 2.92(1, s) 3.75~4.3(2, m) 5.08(4, s) 5.91~6.11(2, m) 6.30(1, d) 6.97(2,d) 7.20(2, m) 7.31~7.63(8, m) 7.68(1, s) 7.84(2, d).

EXAMPLE 27

Preparation of 4-(4-fluoro-phenyloxy)-benzyloxy-cinnamate-5-ethyl norbornene (Cyclic Olefin Compound)

The procedures were performed in the same manner as described in Example 25, excepting that norbornene-5-ethanol was used instead of norbornene-5-ol to prepare 4-(4-fluoro-phenyloxy)-benzyloxy-cinnamate-5-ethyl norbornene.

NMR(CDCl$_3$ (500 MHz), ppm): 0.6(1, m) 1.22~1.27(2, m) 1.36~1.6(3, m) 1.86(1, m) 2.55(1, m) 2.92(1, s) 3.32~3.96(2, m) 5.08(4, s) 5.91~6.11(2, m) 6.30(1, d) 6.97(2,d) 7.20(2, m) 7.31~7.63(8, m) 7.68(1, s) 7.84(2, d).

EXAMPLE 28

Preparation of 4-(4-trifluoromethyl)-benzyloxy-cinnamate-5-norbornene (Cyclic Olefin Compound)

The procedures were performed in the same manner as described in Example 1, excepting that 4-(4-trifluoromethyl)-benzyloxy-benzaldehyde was used instead of 4-benzyloxy-benzaldehyde to prepare 4-(4-trifluoromethyl)-benzyloxy-cinnamate-5-norbornene.

NMR(CDCl$_3$ (500 MHz), ppm): 0.6 (1, m) 1.22~1.27(2, m) 1.47(1,d) 1.88(1, m) 2.67(1, m) 2.93(1, s) 5.05(2, s) 5.97~6.11(2, m) 6.30(1, d) 7.11~7.25(4, m) 7.4(2, m) 7.60~7.68(3, m).

EXAMPLE 29

Preparation of 4-(4-trifluoromethyl)-benzyloxy-cinnamate-5-methyl norbornene (Cyclic Olefin Compound)

The procedures were performed in the same manner as described in Example 28, excepting that norbornene-5-methanol was used instead of norbornene-5-ol to prepare 4-(4-trifluoromethyl)-benzyloxy-cinnamate-5-methyl norbornene.

NMR(CDCl$_3$ (500 MHz), ppm): 0.6(1, m) 1.22~1.27(2, m) 1.47(1,d) 1.88(1, m) 2.47(1, m) 2.93(1, s) 3.74~4.28(2, m) 5.05(2, s) 5.97~6.11(2, m) 6.30(1, d) 7.11~7.25(4, m) 7.4(2, m) 7.60~7.68(3, m).

EXAMPLE 30

Preparation of 4-(4-trifluoromethyl)-benzyloxy-cinnamate-5-ethyl norbornene (Cyclic Olefin Compound)

The procedures were performed in the same manner as described in Example 28, excepting that norbornene-5-ethanol was used instead of norbornene-5-ol to prepare 4-(4-trifluoromethyl)-benzyloxy-cinnamate-5-ethyl norbornene.

NMR(CDCl$_3$ (500 MHz), ppm): 0.6(1, m) 1.22~1.27(2, m) 1.36~1.6(3, m) 1.86(1, m) 2.45(1, m) 2.91(1, s) 3.32~3.96(2, m) 5.05(2, s) 5.97~6.11(2, m) 6.30(1, d) 7.11~7.25(4, m) 7.4(2, m) 7.60~7.68(3, m).

EXAMPLE 31

Preparation of 4-(4-bromo-benzyloxy)-cinnamate-5-norbornene (Cyclic Olefin Compound)

The procedures were performed in the same manner as described in Example 1, excepting that 4-(4-bromo-benzyloxy)-benzaldehyde was used instead of 4-benzyloxy-benzaldehyde to prepare 4-(4-bromo-benzyloxy)-cinnamate-5-norbornene.

NMR(CDCl$_3$ (500 MHz), ppm): 0.6(1, m) 1.22~1.27(2, m) 1.47(1,d) 1.88(1, m) 2.67(1, m) 2.93(1, s) 5.05(2, s) 5.97~6.11(2, m) 6.30(1, d) 6.97(2, d) 7.1(2, m) 7.30(2, m) 7.45(2, d) 7.61(1, s).

Example 32

Preparation of 4-(4-bromo-benzyloxy)-cinnamate-5-methyl norbornene (Cyclic Olefin Compound)

The procedures were performed in the same manner as described in Example 31, excepting that norbornene-5-methanol was used instead of norbornene-5-ol to prepare 4-(4-bromo-benzyloxy)-cinnamate-5-methyl norbornene.

NMR(CDCl$_3$ (500 MHz), ppm): 0.6(1, m) 1.22~1.27(2, m) 1.47(1,d) 1.88(1, m) 2.47(1, m) 2.93(1, s) 3.75~4.3(2, m) 5.05(2, s) 5.97~6.11(2, m) 6.30(1, d) 6.97(2,d) 7.1(2, m) 7.30(2, m) 7.45(2, d) 7.61(1, s).

EXAMPLE 33

Preparation of 4-(4-bromo-benzyloxy)-cinnamate-5-ethyl norbornene (Cyclic Olefin Compound)

The procedures were performed in the same manner as described in Example 31, excepting that norbornene-5-ethanol was used instead of norbornene-5-ol to prepare 4-(4-bromo-benzyloxy)-cinnamate-5-ethyl norbornene.

NMR(CDCl$_3$ (500 MHz), ppm): 0.6(1, m) 1.22~1.27(2, m) 1.36~1.6(3, m) 1.86(1, m) 2.45(1, m) 2.91(1, s) 3.32~3.96(2, m) 5.05(2, s) 5.97~6.11(2, m) 6.30(1, d) 6.97(2,d) 7.1(2, m) 7.30(2, m) 7.45(2, d) 7.61(1, s).

COMPARATIVE EXAMPLE 1

Preparation of 4-methoxy cinnamate-5-norbornene (Cyclic Olefin Compound)

The procedures were performed in the same manner as described in Example 1, excepting that 4-methoxy-benzaldehyde was used instead of 4-benzyloxy-benzaldehyde to prepare 4-methoxy cinnamate-5-norbornene.

NMR(CDCl$_3$ (500 MHz), ppm): 0.66(1, m) 1.22~1.27(2, m) 1.88(1, m) 1.92~1.95(2, m) 2.47(1, m) 3.88(3, s) 3.75~4.3 (2, m) 6.02~6.23(2, m) 6.34~6.40(1, dd) 6.97(2,d) 7.52~7.54 (2, d) 7.66~7.72(1, dd).

COMPARATIVE EXAMPLE 2

Preparation of 4-methylketone cinnamate-5-norbornene (Cyclic Olefin Compound)

The procedures were performed in the same manner as described in Example 1, excepting that 4-methylketone-benzaldehyde was used instead of 4-benzyloxy-benzaldehyde to prepare 4-methylketone cinnamate-5-norbornene.

NMR(CDCl$_3$ (500 MHz), ppm): 0.6(1, m) 1.22~1.27(2, m) 1.47(1,d) 1.88(1, m) 2.67(1, m) 2.93(1, s) 4.3(3, s) 5.97~6.11 (2, m) 6.64(1, d) 7.30~7.39(2, m) 7.63(1, d) 7.70(2, d).

EXAMPLE 34

Polymerization of 4-benzyloxy-cinnamate-5-norbornene

In a 250 ml Schlenk flask were placed 4-benzyloxy-cinnamate-5-norbornene (50 mmol) of Example 1 as a monomer, and purified toluene (400 wt. %) as a solvent. 1-octene (10 mol. %) was also added. Under agitation, the mixture was heated to 90° C. To the flask were added Pd(OAc)$_2$ (16 μmol) and tricyclohexylphosphine (32 μmol) in 1 ml of dichloromethane as a catalyst, and dimethylanilinium tetrakiss(pentafluorophenyl)borate (32 μmol) as a cocatalyst. The mixture was stirred at 90° C. for 16 hours to bring about a reaction.

After completion of the reaction, the reactant mixture was put in an excess of ethanol to obtain a white polymer precipitate. The precipitate was filtered out through a glass funnel to collect a polymer, which was then dried in a vacuum oven at 60° C. for 24 hours to yield a final polymer product (Mw=198 k, PDI=3.22, yield=68%).

EXAMPLE 35

Polymerization of 4-benzyloxy-cinnamate-5-methyl norbornene

The procedures were performed in the same manner as described in Example 34, excepting that 4-benzyloxy-cinnamate-5-methyl norbornene (50 mmol) of Example 2 was used as a monomer instead of 4-benzyloxy-cinnamate-5-norbornene of Example 1 to obtain a polymer product (Mw=162 k, PDI=3.16, yield=81%).

EXAMPLE 36

Polymerization of 4-benzyloxy-cinnamate-5-ethyl norbornene

The procedures were performed in the same manner as described in Example 34, excepting that 4-benzyloxy-cinnamate-5-ethyl norbornene (50 mmol) of Example 3 was used as a monomer instead of 4-benzyloxy-cinnamate-5-norbornene of Example 1 to obtain a polymer product (Mw=159 k, PDI=4.10, yield=80%).

EXAMPLE 37

Polymerization of 4-(4-fluoro-benzyloxy)-cinnamate-5-norbornene

The procedures were performed in the same manner as described in Example 34, excepting that 4-(4-fluoro-benzyloxy)-cinnamate-5-norbornene (50 mmol) of Example 4 was used as a monomer instead of 4-benzyloxy-cinnamate-5-norbornene of Example 1 to obtain a polymer product (Mw=121 k, PDI=3.52, yield=62%).

EXAMPLE 38

Polymerization of 4-(4-fluoro-benzyloxy)-cinnamate-5-methyl norbornene

The procedures were performed in the same manner as described in Example 34, excepting that 4-(4-fluoro-benzyloxy)-cinnamate-5-methyl norbornene (50 mmol) of Example 5 was used as a monomer instead of 4-benzyloxy-cinnamate-5-norbornene of Example 1 to obtain a polymer product (Mw=135 k, PDI=2.94, yield=82%).

EXAMPLE 39

Polymerization of 4-(4-fluoro-benzyloxy)-cinnamate-5-ethyl norbornene

The procedures were performed in the same manner as described in Example 34, excepting that 4-(4-fluoro-benzyloxy)-cinnamate-5-ethyl norbornene (50 mmol) of Example 6 was used as a monomer instead of 4-benzyloxy-cinnamate-5-norbornene of Example 1 to obtain a polymer product (Mw=144 k, PDI=4.03, yield=74%).

EXAMPLE 40

Polymerization of 4-(4-methyl-benzyloxy)-cinnamate-5-norbornene

The procedures were performed in the same manner as described in Example 34, excepting that 4-(4-methyl-benzyloxy)-cinnamate-5-norbornene (50 mmol) of Example 7 was used as a monomer instead of 4-benzyloxy-cinnamate-5-norbornene of Example 1 to obtain a polymer product (Mw=111 k, PDI=3.56, yield=58%).

EXAMPLE 41

Polymerization of 4-(4-methyl-benzyloxy)-cinnamate-5-methyl norbornene

The procedures were performed in the same manner as described in Example 34, excepting that 4-(4-methyl-benzyloxy)-cinnamate-5-methyl norbornene (50 mmol) of Example 8 was used as a monomer instead of 4-benzyloxy-cinnamate-5-norbornene of Example 1 to obtain a polymer product (Mw=134 k, PDI=3.71, yield=75%).

EXAMPLE 42

Polymerization of 4-(4-methyl-benzyloxy)-cinnamate-5-ethyl norbornene

The procedures were performed in the same manner as described in Example 34, excepting that 4-(4-methyl-benzyloxy)-cinnamate-5-ethyl norbornene (50 mmol) of Example 9 was used as a monomer instead of 4-benzyloxy-cinnamate-5-norbornene of Example 1 to obtain a polymer product (Mw=130 k, PDI=4.00, yield=71%).

EXAMPLE 43

Polymerization of 4-(4-methoxy-benzyloxy)-cinnamate-5-norbornene

The procedures were performed in the same manner as described in Example 34, excepting that 4-(4-methoxy-benzyloxy)-cinnamate-5-norbornene (50 mmol) of Example 10 was used as a monomer instead of 4-benzyloxy-cinnamate-5-norbornene of Example 1 to obtain a polymer product (Mw=146 k, PDI=3.42, yield=74%).

EXAMPLE 44

Polymerization of 4-(4-methoxy-benzyloxy)-cinnamate-5-methyl norbornene

The procedures were performed in the same manner as described in Example 34, excepting that 4-(4-methoxy-benzyloxy)-cinnamate-5-methyl norbornene (50 mmol) of Example 11 was used as a monomer instead of 4-benzyloxy-cinnamate-5-norbornene of Example 1 to obtain a polymer product (Mw=144k, PDI=3.04, yield=79%).

EXAMPLE 45

Polymerization of 4-(4-methoxy-benzyloxy)-cinnamate-5-ethyl norbornene

The procedures were performed in the same manner as described in Example 34, excepting that 4-(4-methoxy-benzyloxy)-cinnamate-5-ethyl norbornene (50 mmol) of Example 12 was used as a monomer instead of 4-benzyloxy-cinnamate-5-norbornene of Example 1 to obtain a polymer product (Mw=123 k, PDI=3.69, yield=71%).

EXAMPLE 46

Polymerization of 4-(2-naphthalene-methyloxy)-cinnamate-5-norbornene

The procedures were performed in the same manner as described in Example 34, excepting that 4-(2-naphthalene-methyloxy)-cinnamate-5-norbornene (50 mmol) of Example 13 was used as a monomer instead of 4-benzyloxy-cinnamate-5-norbornene of Example 1 to obtain a polymer product (Mw=91 k, PDI=4.01, yield=54%).

EXAMPLE 47

Polymerization of
4-(2-naphthalene-methyloxy)-cinnamate-5-methyl norbornene

The procedures were performed in the same manner as described in Example 34, excepting that 4-(2-naphthalene-methyloxy)-cinnamate-5-methyl norbornene (50 mmol) of Example 14 was used as a monomer instead of 4-benzyloxy-cinnamate-5-norbornene of Example 1 to obtain a polymer product (Mw=83 k, PDI=3.97, yield=61%).

EXAMPLE 48

Polymerization of
4-(2-naphthalene-methyloxy)-cinnamate-5-ethyl norbornene

The procedures were performed in the same manner as described in Example 34, excepting that 4-(2-naphthalene-methyloxy)-cinnamate-5-ethyl norbornene (50 mmol) of Example 15 was used as a monomer instead of 4-benzyloxy-cinnamate-5-norbornene of Example 1 to obtain a polymer product (Mw=102 k, PDI=3.72, yield=43%).

EXAMPLE 49

Polymerization of 4-(4-methylketone benzyloxy)-cinnamate-5-norbornene

The procedures were performed in the same manner as described in Example 34, excepting that 4-(4-methylketone benzyloxy)-cinnamate-5-norbornene (50 mmol) of Example 16 was used as a monomer instead of 4-benzyloxy-cinnamate-5-norbornene of Example 1 to obtain a polymer product (Mw=109 k, PDI=4.23, yield=47%).

EXAMPLE 50

Polymerization of 4-(4-methylketone benzyloxy)-cinnamate-5-methyl norbornene

The procedures were performed in the same manner as described in Example 34, excepting that 4-(4-methylketone benzyloxy)-cinnamate-5-methyl norbornene (50 mmol) of Example 17 was used as a monomer instead of 4-benzyloxy-cinnamate-5-norbornene of Example 1 to obtain a polymer product (Mw=111 k, PDI=4.21, yield=51%).

EXAMPLE 51

Polymerization of 4-(4-methylketone benzyloxy)-cinnamate-5-ethyl norbornene

The procedures were performed in the same manner as described in Example 34, excepting that 4-(4-methylketone benzyloxy)-cinnamate-5-ethyl norbornene (50 mmol) of Example 18 was used as a monomer instead of 4-benzyloxy-cinnamate-5-norbornene of Example 1 to obtain a polymer product (Mw=87 k, PDI=3.32, yield=43%).

EXAMPLE 52

Polymerization of 4-(1-phenyl perfluoroheptyloxy)-cinnamate-5-norbornene

The procedures were performed in the same manner as described in Example 34, excepting that 4-(1-phenyl perfluoroheptyloxy)-cinnamate-5-norbornene (50 mmol) of Example 19 was used as a monomer instead of 4-benzyloxy-cinnamate-5-norbornene of Example 1 to obtain a polymer product (Mw=116 k, PDI=3.09, yield=57%).

EXAMPLE 53

Polymerization of 4-(1-phenyl perfluoroheptyloxy)-cinnamate-5-methyl norbornene

The procedures were performed in the same manner as described in Example 34, excepting that 4-(1-phenyl perfluoroheptyloxy)-cinnamate-5-methyl norbornene (50 mmol) of Example 20 was used as a monomer instead of 4-benzyloxy-cinnamate-5-norbornene of Example 1 to obtain a polymer product (Mw=105 k, PDI=3.88, yield=69%).

EXAMPLE 54

Polymerization of 4-(1-phenyl perfluoroheptyloxy)-cinnamate-5-ethyl norbornene

The procedures were performed in the same manner as described in Example 34, excepting that 4-(1-phenyl perfluoroheptyloxy)-cinnamate-5-ethyl norbornene (50 mmol) of Example 21 was used as a monomer instead of 4-benzyloxy-cinnamate-5-norbornene of Example 1 to obtain a polymer product (Mw=87 k, PDI=4.62, yield=51%).

EXAMPLE 55

Polymerization of
4-(4-benzyloxy)-benzyloxy-cinnamate-5-norbornene

The procedures were performed in the same manner as described in Example 34, excepting that 4-(4-benzyloxy)-benzyloxy-cinnamate-5-norbornene (50 mmol) of Example 22 was used as a monomer instead of 4-benzyloxy-cinnamate-5-norbornene of Example 1 to obtain a polymer product (Mw=137 k, PDI=3.19, yield=68%).

EXAMPLE 56

Polymerization of
4-(4-benzyloxy)-benzyloxy-cinnamate-5-methyl norbornene

The procedures were performed in the same manner as described in Example 34, excepting that 4-(4-benzyloxy)-benzyloxy-cinnamate-5-methyl norbornene (50 mmol) of Example 23 was used as a monomer instead of 4-benzyloxy-cinnamate-5-norbornene of Example 1 to obtain a polymer product (Mw=121 k, PDI=3.52, yield=74%).

EXAMPLE 57

Polymerization of
4-(4-benzyloxy)-benzyloxy-cinnamate-5-ethyl norbornene

The procedures were performed in the same manner as described in Example 34, excepting that 4-(4-benzyloxy)-benzyloxy-cinnamate-5-ethyl norbornene (50 mmol) of Example 24 was used as a monomer instead of 4-benzyloxy-cinnamate-5-norbornene of Example 1 to obtain a polymer product (Mw=130 k, PDI=4.67, yield=63%).

EXAMPLE 58

Polymerization of 4-(4-fluoro-phenyloxy)-benzyloxy-cinnamate-5-norbornene

The procedures were performed in the same manner as described in Example 34, excepting that 4-(4-fluoro-phenyloxy)-benzyloxy-cinnamate-5-norbornene (50 mmol) of Example 25 was used as a monomer instead of 4-benzyloxy-cinnamate-5-norbornene of Example 1 to obtain a polymer product (Mw=154 k, PDI=3.22, yield=72%).

EXAMPLE 59

Polymerization of 4-(4-fluoro-phenyloxy)-benzyloxy-cinnamate-5-methyl norbornene The procedures were performed in the same manner as described in Example 34, excepting that 4-(4-fluoro-phenyloxy)-benzyloxy-cinnamate-5-methyl norbornene (50 mmol) of Example 26 was used as a monomer instead of 4-benzyloxy-cinnamate-5-norbornene of Example 1 to obtain a polymer product (Mw=148 k, PDI=3.61, yield=73%).

EXAMPLE 60

Polymerization of 4-(4-fluoro-phenyloxy)-benzyloxy-cinnamate-5-ethyl norbornene

The procedures were performed in the same manner as described in Example 34, excepting that 4-(4-fluoro-phenyloxy)-benzyloxy-cinnamate-5-ethyl norbornene (50 mmol) of Example 27 was used as a monomer instead of 4-benzyloxy-cinnamate-5-norbornene of Example 1 to obtain a polymer product (Mw=116 k, PDI=4.17, yield=68%).

EXAMPLE 61

Polymerization of 4-(4-trifluoromethyl)-benzyloxy-cinnamate-5-norbornene

The procedures were performed in the same manner as described in Example 34, excepting that 4-(4-trifluoromethyl)-benzyloxy-cinnamate-5-norbornene (50 mmol) of Example 28 was used as a monomer instead of 4-benzyloxy-cinnamate-5-norbornene of Example 1 to obtain a polymer product (Mw=133 k, PDI=3.10, yield=44%).

EXAMPLE 62

Polymerization of 4-(4-trifluoromethyl)-benzyloxy-cinnamate-5-methyl norbornene

The procedures were performed in the same manner as described in Example 34, excepting that 4-(4-trifluoromethyl)-benzyloxy-cinnamate-5-methyl norbornene (50 mmol) of Example 29 was used as a monomer instead of 4-benzyloxy-cinnamate-5-norbornene of Example 1 to obtain a polymer product (Mw=121 k, PDI=3.38, yield=48%).

EXAMPLE 63

Polymerization of 4-(4-trifluoromethyl)-benzyloxy-cinnamate-5-ethyl norbornene

The procedures were performed in the same manner as described in Example 34, excepting that 4-(4-trifluoromethyl)-benzyloxy-cinnamate-5-ethyl norbornene (50 mmol) of Example 30 was used as a monomer instead of 4-benzyloxy-cinnamate-5-norbornene of Example 1 to obtain a polymer product (Mw=127 k, PDI=3.32, yield=41%).

EXAMPLE 64

Polymerization of 4-(4-bromo-benzyloxy)-cinnamate-5-norbornene

The procedures were performed in the same manner as described in Example 34, excepting that 4-(4-bromo-benzyloxy)-cinnamate-5-norbornene (50 mmol) of Example 31 was used as a monomer instead of 4-benzyloxy-cinnamate-5-norbornene of Example 1 to obtain a polymer product (Mw=168 k, PDI=3.06, yield=74%).

EXAMPLE 65

Polymerization of 4-(4-bromo-benzyloxy)-cinnamate-5-methyl norbornene

The procedures were performed in the same manner as described in Example 34, excepting that 4-(4-bromo-benzyloxy)-cinnamate-5-methyl norbornene (50 mmol) of Example 32 was used as a monomer instead of 4-benzyloxy-cinnamate-5-norbornene of Example 1 to obtain a polymer product (Mw=160 k, PDI=3.24, yield=83%).

EXAMPLE 66

Polymerization of 4-(4-bromo-benzyloxy)-cinnamate-5-ethyl norbornene

The procedures were performed in the same manner as described in Example 34, excepting that 4-(4-bromo-benzyloxy)-cinnamate-5-ethyl norbornene (50 mmol) of Example 33 was used as a monomer instead of 4-benzyloxy-cinnamate-5-norbornene of Example 1 to obtain a polymer product (Mw=146 k, PDI=3.52, yield=72%).

COMPARATIVE EXAMPLE 3

Polymerization of 4-methoxy cinnamate-5-norbornene

The procedures were performed in the same manner as described in Example 34, excepting that 4-methoxy cinnamate-5-norbornene (50 mmol) of Comparative Example 1 was used as a monomer instead of 4-benzyloxy-cinnamate-5-norbornene of Example 1 to obtain a polymer product (Mw=133 k, PDI=3.11, yield=86%).

COMPARATIVE EXAMPLE 4

Polymerization of 4-methylketone cinnamate-5-norbornene

The procedures were performed in the same manner as described in Example 34, excepting that 4-methylketone cinnamate-5-norbornene (50 mmol) of Comparative Example 2 was used as a monomer instead of 4-benzyloxy-cinnamate-5-norbornene of Example 1 to obtain a polymer product (Mw=157 k, PDI=3.52, yield=81%).

EXAMPLE 67

Polymer Preparation Using Ring-Opening Methathesis Polymerization and Hydrogenation of 4-Benzyloxy-Cinnamate-5-Norbornene In a 250 ml Schlenk flask in the Ar atmosphere were placed 4-benzyloxy-cinnamate-5-norbornene (50 mmol) and then purified toluene (600 wt. %) as a solvent. With the flask maintained at a polymerization temperature of 80° C., triethyl aluminum (1 mmol) was added as a cocatalyst. Subsequently, to the flask was added 1 ml (WCl$_6$: 0.01 mmol, ethanol: 0.03 mmol) of a 0.01M (mol/L) toluene solution containing a mixture of tungsten hexachloride (WCl$_6$) and ethanol at a mixing ratio of 1:3. Finally, 1-octene (15 mol. %) was added as a molecular weight modifier to the flask, which was then stirred at 80° C. for 18 hours to bring about a reaction. After completion of the reaction, a small amount of ethyl vinyl ether as a polymerization inhibitor was added dropwise to the polymerization solution, and the flask was stirred for 5 minutes.

With the polymerization solution transferred to a 300 mL high-pressure reactor, 0.06 ml of triethyl aluminum (TEA) was added to the solution. Subsequently, 0.50 g of grace raney nickel (slurry phase in water) was added, and the solution was stirred at 150° C. for 2 hours under the hydrogen pressure maintained at 80 atm to bring about a reaction. After completion of the reaction, the polymerization solution was added dropwise to acetone to cause precipitation. The precipitate thus obtained was filtered out and dried in a vacuum oven at 70° C. for 15 hours, thereby obtaining a ring-opened hydrogenated polymer of 4-benzyloxy-cinnamate-5-norbornene (Mw=83 k, PDI=4.92, yield=88%).

EXAMPLE 68

Polymer Preparation Using Ring-Opening Methathesis Polymerization and Hydrogenation of 4-Benzyloxy-Cinnamate-5-Methyl Norbornene The procedures were performed in the same manner as described in Example 67, excepting that 4-benzyloxy-cinnamate-5-methyl norbornene (50 mmol) of Example 2 was used as a monomer instead of 4-benzyloxy-cinnamate-5-norbornene of Example 1 to form a polymer (Mw=87 k, PDI=4.22, yield=87%).

EXAMPLE 69

Polymer Preparation Using Ring-Opening Methathesis Polymerization and Hydrogenation of 4-Benzyloxy-Cinnamate-5-Ethyl Norbornene The procedures were performed in the same manner as described in Example 67, excepting that 4-benzyloxy-cinnamate-5-ethyl norbornene (50 mmol) of Example 3 was used as a monomer instead of 4-benzyloxy-cinnamate-5-norbornene of Example 1 to form a polymer (Mw=71 k, PDI=4.18, yield=80%).

EXAMPLE 70

Polymer Preparation Using Ring-Opening Methathesis Polymerization and Hydrogenation of 4-(4-Fluoro-Benzyloxy)-Cinnamate-5-Norbornene The procedures were performed in the same manner as described in Example 67, excepting that 4-(4-fluoro-benzyloxy)-cinnamate-5-norbornene (50 mmol) of Example 4 was used as a monomer instead of 4-benzyloxy-cinnamate-5-norbornene of Example 1 to form a polymer (Mw=90 k, PDI=3.40, yield=71%).

EXAMPLE 71

Polymer Preparation Using Ring-Opening Methathesis Polymerization and Hydrogenation of 4-(4-Fluoro-Benzyloxy)-Cinnamate-5-Methyl Norbornene The procedures were performed in the same manner as described in Example 67, excepting that 4-(4-fluoro-benzyloxy)-cinnamate-5-methyl norbornene (50 mmol) of Example 5 was used as a monomer instead of 4-benzyloxy-cinnamate-5-norbornene of Example 1 to form a polymer (Mw=87 k, PDI=3.98, yield=76%).

EXAMPLE 72

Polymer Preparation Using Ring-Opening Methathesis Polymerization and Hydrogenation of 4-(4-Fluoro-Benzyloxy)-Cinnamate-5-Ethyl Norbornene The procedures were performed in the same manner as described in Example 67, excepting that 4-(4-fluoro-benzyloxy)-cinnamate-5-ethyl norbornene (50 mmol) of Example 6 was used as a monomer instead of 4-benzyloxy-cinnamate-5-norbornene of Example 1 to form a polymer (Mw=68 k, PDI=3.51, yield=74%).

EXAMPLE 73

Polymer Preparation Using Ring-Opening Methathesis Polymerization and Hydrogenation of 4-(4-Methyl-Benzyloxy)-Cinnamate-5-Norbornene The procedures were performed in the same manner as described in Example 67, excepting that 4-(4-methyl-benzyloxy)-cinnamate-5-norbornene (50 mmol) of Example 7 was used as a monomer instead of 4-benzyloxy-cinnamate-5-norbornene of Example 1 to form a polymer (Mw=69 k, PDI=4.13, yield=77%).

EXAMPLE 74

Polymer Preparation Using Ring-Opening Methathesis Polymerization and Hydrogenation of 4-(4-Methyl-Benzyloxy)-Cinnamate-5-Methyl Norbornene The procedures were performed in the same manner as described in Example 67, excepting that 4-(4-methyl-benzyloxy)-cinnamate-5-methyl norbornene (50 mmol) of Example 8 was used as a monomer instead of 4-benzyloxycinnamate-5-norbornene of Example 1 to form a polymer (Mw=81 k, PDI=3.49, yield=84%).

EXAMPLE 75

Polymer Preparation Using Ring-Opening Methathesis Polymerization and Hydrogenation of 4-(4-Methyl-Benzyloxy)-Cinnamate-5-Ethyl Norbornene The procedures were performed in the same manner as described in Example 67, excepting that 4-(4-methyl-benzyloxy)-cinnamate-5-ethyl norbornene (50 mmol) of Example 9 was used as a monomer instead of 4-benzyloxy-cinnamate-5-norbornene of Example 1 to form a polymer (Mw=55 k, PDI=5.37, yield=68%).

EXAMPLE 76

Polymer Preparation Using Ring-Opening Methathesis Polymerization and Hydrogenation of 4-(4-Methoxy-Benzyloxy)-Cinnamate-5-Norbornene The procedures were performed in the same manner as described in Example 67, excepting that 4-(4-methoxy-benzyloxy)-cinnamate-5-norbornene (50 mmol) of Example 10 was used as a monomer instead of 4-benzyloxy-cinnamate-5-norbornene of Example 1 to form a polymer (Mw=88 k, PDI=3.56, yield=84%).

EXAMPLE 77

Polymer Preparation Using Ring-Opening Methathesis Polymerization and Hydrogenation of 4-(4-Methoxy-Benzyloxy)-Cinnamate-5-Methyl Norbornene The procedures were performed in the same manner as described in Example 67, excepting that 4-(4-methoxy-benzyloxy)-cinnamate-5-methyl norbornene (50 mmol) of Example 11 was used as a monomer instead of 4-benzyloxy-cinnamate-5-norbornene of Example 1 to form a polymer (Mw=81 k, PDI=3.14, yield=80%).

EXAMPLE 78

Polymer Preparation Using Ring-Opening Methathesis Polymerization and Hydrogenation of 4-(4-Methoxy-Benzyloxy)-Cinnamate-5-Ethyl Norbornene The procedures were performed in the same manner as described in Example 67, excepting that 4-(4-methoxy-benzyloxy)-cinnamate-5-ethyl norbornene (50 mmol) of Example 12 was used as a monomer instead of 4-benzyloxy-cinnamate-5-norbornene of Example 1 to form a polymer (Mw=84 k, PDI=3.90, yield=73%).

EXAMPLE 79

Polymer Preparation Using Ring-Opening Methathesis Polymerization and Hydrogenation of 4-(2-Naphthalene-Methyloxy)-Cinnamate-5-Norbornene The procedures were performed in the same manner as described in Example 67, excepting that 4-(2-naphthalene-methyloxy)-cinnamate-5-norbornene (50 mmol) of Example 13 was used as a monomer instead of 4-benzyloxy-cinnamate-5-norbornene of Example 1 to form a polymer (Mw=49 k, PDI=4.53, yield=55%).

EXAMPLE 80

Polymer Preparation Using Ring-Opening Methathesis Polymerization and Hydrogenation of 4-(2-Naphthalene-Methyloxy)-Cinnamate-5-Methyl Norbornene The procedures were performed in the same manner as described in Example 67, excepting that 4-(2-naphthalene-methyloxy)-cinnamate-5-methyl norbornene (50 mmol) of Example 14 was used as a monomer instead of 4-benzyloxy-cinnamate-5-norbornene of Example 1 to form a polymer (Mw=53 k, PDI=3.91, yield=51%).

EXAMPLE 81

Polymer Preparation Using Ring-Opening Methathesis Polymerization and Hydrogenation of 4-(2-Naphthalene-Methyloxy)-Cinnamate-5-Ethyl Norbornene The procedures were performed in the same manner as described in Example 67, excepting that 4-(2-naphthalene-methyloxy)-cinnamate-5-ethyl norbornene (50 mmol) of Example 15 was used as a monomer instead of 4-benzyloxy-cinnamate-5-norbornene of Example 1 to form a polymer (Mw=59 k, PDI=3.99, yield=54%).

EXAMPLE 82

Polymer Preparation Using Ring-Opening Methathesis Polymerization and Hydrogenation of 4-(4-Methylketone Benzyloxy)-Cinnamate-5-Norbornene The procedures were performed in the same manner as described in Example 67, excepting that 4-(4-methylketone benzyloxy)-cinnamate-5-norbornene (50 mmol) of Example 16 was used as a monomer instead of 4-benzyloxy-cinnamate-5-norbornene of Example 1 to form a polymer (Mw=93 k, PDI=3.49, yield=88%).

EXAMPLE 83

Polymer Preparation Using Ring-Opening Methathesis Polymerization and Hydrogenation of 4-(4-Methylketone Benzyloxy)-Cinnamate-5-Methyl Norbornene The procedures were performed in the same manner as described in Example 67, excepting that 4-(4-methylketone benzyloxy)-cinnamate-5-methyl norbornene (50 mmol) of Example 17 was used as a monomer instead of 4-benzyloxy-cinnamate-5-norbornene of Example 1 to form a polymer (Mw=85 k, PDI=4.26, yield=81%).

EXAMPLE 84

Polymer Preparation Using Ring-Opening Methathesis Polymerization and Hydrogenation of 4-(4-Methylketone Benzyloxy)-Cinnamate-5-Ethyl Norbornene The procedures were performed in the same manner as described in Example 67, excepting that 4-(4-methylketone benzyloxy)-cinnamate-5-ethyl norbornene (50 mmol) of Example 18 was used as a monomer instead of 4-benzyloxy-cinnamate-5-norbornene of Example 1 to form a polymer (Mw=94 k, PDI=4.56, yield=71%).

EXAMPLE 85

Polymer Preparation Using Ring-Opening Methathesis Polymerization and Hydrogenation of 4-(1-Phenyl Perfluoroheptyloxy)-Cinnamate-5-Norbornene The procedures were performed in the same manner as described in Example 67, excepting that 4-(1-phenyl perfluoroheptyloxy)-cinnamate-5-norbornene (50 mmol) of Example 19 was used as a monomer instead of 4-benzyloxy-cinnamate-5-norbornene of Example 1 to form a polymer (Mw=42 k, PDI=4.37, yield=54%).

EXAMPLE 86

Polymer Preparation Using Ring-Opening Methathesis Polymerization and Hydrogenation of 4-(1-Phenyl Perfluoroheptyloxy)-Cinnamate-5-Methyl Norbornene The procedures were performed in the same manner as described in Example 67, excepting that 4-(1-phenyl perfluoroheptyloxy)-cinnamate-5-methyl norbornene (50 mmol) of Example 20 was used as a monomer instead of 4-benzyloxy-cinnamate-5-norbornene of Example 1 to form a polymer (Mw=45 k, PDI=3.92, yield=52%).

EXAMPLE 87

Polymer Preparation Using Ring-Opening Methathesis Polymerization and Hydrogenation of 4-(1-Phenyl Perfluoroheptyloxy)-Cinnamate-5-Ethyl Norbornene The procedures were performed in the same manner as described in Example 67, excepting that 4-(1-phenyl perfluoroheptyloxy)-cinnamate-5-ethyl norbornene (50 mmol) of Example 21 was used as a monomer instead of 4-benzyloxy-cinnamate-5-norbornene of Example 1 to form a polymer (Mw=44 k, PDI=4.52, yield=43%).

EXAMPLE 88

Polymer Preparation Using Ring-Opening Methathesis Polymerization and Hydrogenation of 4-(4-Benzyloxy)-Benzyloxy-Cinnamate-5-Norbornene The procedures were performed in the same manner as described in Example 67, excepting that 4-(4-benzyloxy)-benzyloxy-cinnamate-5-norbornene (50 mmol) of Example 22 was used as a monomer instead of 4-benzyloxy-cinnamate-5-norbornene of Example 1 to form a polymer (Mw=82 k, PDI=3.44, yield=70%).

EXAMPLE 89

Polymer Preparation Using Ring-Opening Methathesis Polymerization and Hydrogenation of 4-(4-Benzyloxy)-Benzyloxy-Cinnamate-5-Methyl Norbornene The procedures were performed in the same manner as described in Example 67, excepting that 4-(4-benzyloxy)-benzyloxy-cinnamate-5-methyl norbornene (50 mmol) of Example 23 was used as a monomer instead of 4-benzyloxy-cinnamate-5-norbornene of Example 1 to form a polymer (Mw=76 k, PDI=3.67, yield=73%).

EXAMPLE 90

Polymer Preparation Using Ring-Opening Methathesis Polymerization and Hydrogenation of 4-(4-Benzyloxy)-Benzyloxy-Cinnamate-5-Ethyl Norbornene The procedures were performed in the same manner as described in Example 67, excepting that 4-(4-benzyloxy)-benzyloxy-cinnamate-5-ethyl norbornene (50 mmol) of Example 24 was used as a monomer instead of 4-benzyloxy-cinnamate-5-norbornene of Example 1 to form a polymer (Mw=68 k, PDI=4.81, yield=65%).

EXAMPLE 91

Polymer Preparation Using Ring-Opening Methathesis Polymerization and Hydrogenation of 4-(4-Fluoro-Phenyloxy)-Benzyloxy-Cinnamate-5-Norbornene The procedures were performed in the same manner as described in Example 67, excepting that 4-(4-fluoro-phenyloxy)-benzyloxy-cinnamate-5-norbornene (50 mmol) of Example 25 was used as a monomer instead of 4-benzyloxy-cinnamate-5-norbornene of Example 1 to form a polymer (Mw=51 k, PDI=4.72, yield=41%).

EXAMPLE 92

Polymer Preparation Using Ring-Opening Methathesis Polymerization and Hydrogenation of 4-(4-Fluoro-Phenyloxy)-Benzyloxy-Cinnamate-5-Methyl Norbornene The procedures were performed in the same manner as described in Example 67, excepting that 4-(4-fluoro-phenyloxy)-benzyloxy-cinnamate-5-methyl norbornene (50 mmol) of Example 26 was used as a monomer instead of 4-benzyloxy-cinnamate-5-norbornene of Example 1 to form a polymer (Mw=55 k, PDI=4.13, yield=47%).

EXAMPLE 93

Polymer Preparation Using Ring-Opening Methathesis Polymerization and Hydrogenation of 4-(4-Fluoro-Phenyloxy)-Benzyloxy-Cinnamate-5-Ethyl Norbornene The procedures were performed in the same manner as described in Example 67, excepting that 4-(4-fluoro-phenyloxy)-benzyloxy-cinnamate-5-ethyl norbornene (50 mmol) of Example 27 was used as a monomer instead of 4-benzyloxy-cinnamate-5-norbornene of Example 1 to form a polymer (Mw=49 k, PDI=4.11, yield=42%).

Example 94

Polymer Preparation Using Ring-Opening Methathesis Polymerization and Hydrogenation of 4-(4-Trifluoromethyl)-Benzyloxy-Cinnamate-5-Norbornene The procedures were performed in the same manner as described in Example 67, excepting that 4-(4-trifluoromethyl)-benzyloxy-cinnamate-5-norbornene (50 mmol) of Example 28 was used as a monomer instead of 4-benzyloxy-cinnamate-5-norbornene of Example 1 to form a polymer (Mw=53 k, PDI=3.01, yield=56%).

EXAMPLE 95

Polymer Preparation Using Ring-Opening Methathesis Polymerization and Hydrogenation of 4-(4-Trifluoromethyl)-Benzyloxy-Cinnamate-5-Methyl Norbornene The procedures were performed in the same manner as described in Example 67, excepting that 4-(4-trifluoromethyl)-benzyloxy-cinnamate-5-methyl norbornene (50 mmol) of Example 29 was used as a monomer instead of 4-benzyloxy-cinnamate-5-norbornene of Example 1 to form a polymer (Mw=72 k, PDI=3.95, yield=55%).

EXAMPLE 96

Polymer Preparation Using Ring-Opening Methathesis Polymerization and Hydrogenation of 4-(4-Trifluoromethyl)-Benzyloxy-Cinnamate-5-Ethyl Norbornene The procedures were performed in the same manner as described in Example 67, excepting that 4-(4-trifluoromethyl)-benzyloxy-cinnamate-5-ethyl norbornene (50 mmol) of Example 30 was used as a monomer instead of 4-benzyloxy-cinnamate-5-norbornene of Example 1 to form a polymer (Mw=59 k, PDI=3.72, yield=50%).

EXAMPLE 97

Polymer Preparation Using Ring-Opening Methathesis Polymerization and Hydrogenation of 4-(4-Bromo-Benzyloxy)-Cinnamate-5-Norbornene The procedures were performed in the same manner as described in Example 67, excepting that 4-(4-bromo-benzyloxy)-cinnamate-5-norbornene (50 mmol) of Example 31 was used as a monomer instead of 4-benzyloxy-cinnamate-5-norbornene of Example 1 to form a polymer (Mw=97 k, PDI=3.14, yield=80%).

EXAMPLE 98

Polymer Preparation Using Ring-Opening Methathesis Polymerization and Hydrogenation of 4-(4-Bromo-Benzyloxy)-Cinnamate-5-Methyl Norbornene The procedures were performed in the same manner as described in Example 67, excepting that 4-(4-bromo-benzyloxy)-cinnamate-5-methyl norbornene (50 mmol) of Example 32 was used as a monomer instead of 4-benzyloxy-cinnamate-5-norbornene of Example 1 to form a polymer (Mw=93 k, PDI=3.28, yield=83%).

EXAMPLE 99

Polymer Preparation Using Ring-Opening Methathesis Polymerization and Hydrogenation of 4-(4-Bromo-Benzyloxy)-Cinnamate-5-Ethyl Norbornene The procedures were performed in the same manner as described in Example 67, excepting that 4-(4-bromo-benzyloxy)-cinnamate-5-ethyl norbornene (50 mmol) of Example 33 was used as a monomer instead of 4-benzyloxy-cinnamate-5-norbornene of Example 1 to form a polymer (Mw=88 k, PDI=3.93, yield=81%).

EXPERIMENTAL EXAMPLE 1

Fabrication of Liquid Crystal Film 2 to 3 wt. % of each photoreactive polymer of Examples 34 to 99 and Comparative Examples 3 and 4, 0.5 to 1.0 wt. % of a binder (i.e., an acryl-based binder of PETA, DPHA or triacryl isocyanurate), and 0.05 to 1 wt. % of a photo-initiator (Irgacure 907, Ciba) were dissolved in a toluene solvent, and the resultant solution was put dropwise on a glass substrate or a polymer film (i.e., a cyclic olefin-based oriented film or a TAC film) for bar coating. The bar-coated film was dried at 80° C. for 2 min. and exposed to polarized UV radiation. To ascertain that the director orientation of liquid crystals is changed, the cured alignment layer half covered was rotated by 90 degrees and exposed to the polarized UV radiation again. The exposure amount of the polarized UV radiation was regulated by the exposure time. A-plate liquid crystal (25 wt. % in toluene) was put dropwise on the alignment layer for bar coating, dried at 60° C. for 2 min. and exposed to 20 mJ of UV radiation for curing.

Figure 2:
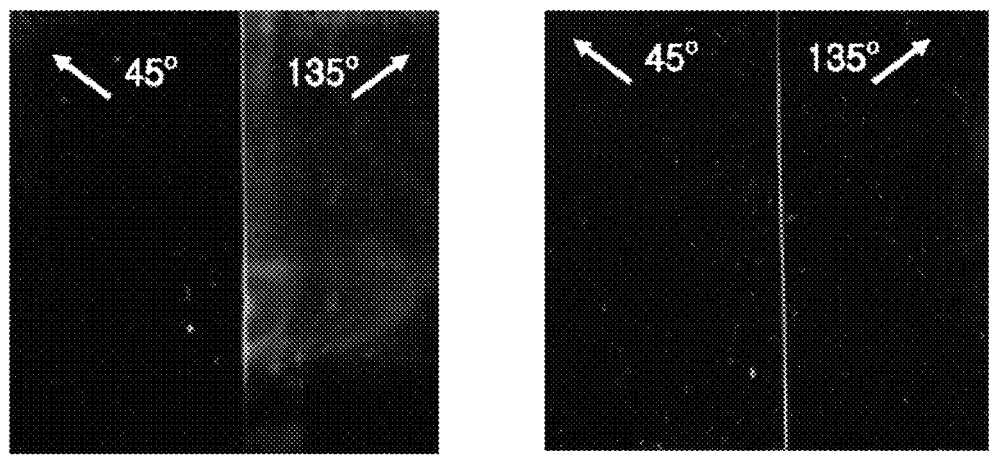
FIG. 2 shows photographs of alignment layers using the polymers of Comparative Example and Example in experimental examples after first and second alignments achieved by changing the polarization direction.

FIG. 2 shows the images of alignment layers, that is, a first oriented alignment layer (45 •) before 90-degree rotation and a second oriented alignment layer (135 •) after 90-degree rotation between polarizers. The left-sided picture of FIG. 2 shows the alignment layer using the polymer of Comparative Example 3 (monomer: Comparative Example 1) as a photo-aligned substance after the second alignment, the right-sided picture showing the alignment layer using the polymer of Example 39 (monomer: Example 6) as a photo-aligned substance after the second alignment. The pictures were taken of the films between two crossed polarizers.

Referring to FIG. 2, the alignment layer using the polymer of Comparative Example 3 hardly had a change in the alignment direction upon a change of the polarization direction during the second alignment, causing alignment errors. In contrast, the alignment layer using the polymer of Example 39 was ready to change the alignment direction upon a change of the polarization direction during the second alignment, acquiring a good image. The reason of this result seems likely to be that the bulky aralkyl structure at the ends of the photoreactive groups in the polymer of the Example 39 supports the formation of a large free volume between adjacent photoreactive groups, thereby providing the alignment layer with readiness for change in the alignment direction according to the polarization direction as well as excellences in photoreactivity, alignment, and alignment rate.

Figure 3:
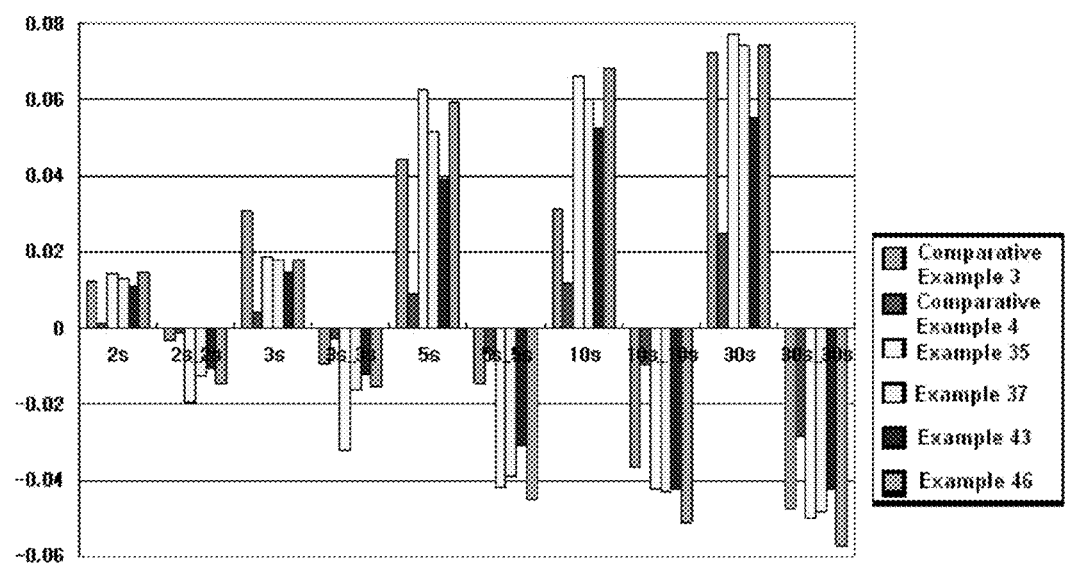
FIG. 3 show graphs describing the change of anisotropy of alignment layers using the polymers of Comparative Examples and Examples in experimental examples after first and second alignments achieved by changing the polarization direction.

The same procedures as described in regard to FIG. 2 were carried out to cause first and second alignments on the alignment layers using the polymers of Examples 35, 37, 43 and 46 (monomer: Examples 2, 4, 10 and 13) and Comparative Examples 3 and 4 (monomer: Comparative Examples 1 and 2) to measure the change of anisotropy. The first and second alignments were carried out on the alignment layers five times each, while varying the irradiation time as 2 sec. (that is, performing a two-second exposure for the first alignment and, after changing the alignment direction, a two-second exposure for the second alignment), 3 sec., 5 sec., 10 sec. and 30 sec. The change of anisotropy as can be seen from the experiment results is depicted as the graphs of FIG. 3. Referring to FIG. 3, the first and second leftmost graphs show the change of anisotropy after first and second alignments using a two-second exposure, and the third and fourth graphs, the fifth and sixth graphs, the seventh and eighth graphs, and ninth and tenth graphs show the change of anisotropy after first and second alignments using three-second, five-second, ten-second and thirty-second exposures, respectively.

The change of anisotropy was measured by means of UV absorbance. For anisotropy measurement, polarizers were arranged in a UV-vis spectrometer to determine absorbance A(parallel) and absorbance A(perpendicular) and calculate $DR=(A(\|)-A(\bot))/(A(\|)+A(\bot))$, where the reference wavelength was 310 nm.

Referring to FIG. 3, the alignment layer using the polymer of Comparative Example 4 had an insignificant change of anisotropy under UV radiation, consequently with poor alignment. The alignment layer using the polymer of Comparative Example 3 had a little change of anisotropy after the first alignment, with a considerably great drop in the absolute value of anisotropy after the second alignment. This means that the change of anisotropy after the second alignment is not easy to achieve, thereby possibly causing alignment errors when liquid crystals are put dropwise on the alignment layer.

In contrast, the alignment layers using the polymers according to the examples had only a little drop in the absolute value of anisotropy even after the second alignment and showed an anisotropic characteristic with readiness for change in alignment direction. This demonstrates the fact that the polymers of the examples possess not only excellences in alignment and alignment rate but also readiness for change in alignment direction depending on the change of the polarization direction.

What is claimed is:
1. An alignment layer comprising a photoreactive polymer, wherein the photoreactive polymer comprises a repeating unit of the following formula 3a or 3b, and has a weight average molecular weight of 91,000 to 1,000,000:

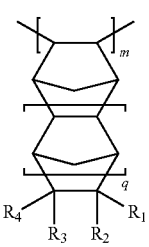

[Formula 3a]

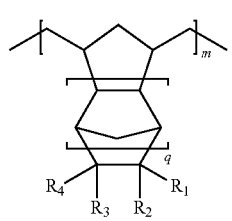

[Formula 3b]

wherein independently, m is 50 to 5,000;
q is an integer from 0 to 4; and
at least one of R1, R2, R3 and R4 is any one selected from the group consisting of radicals of the following formula 1a and 1b,
among the R1 to R4, the remainders other than the radical of the formula 1a or 1b are the same as or different from one another and independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; and a polar functional group comprising at least one of oxygen, nitrogen, phosphor, sulfur, silicon, and boron,
when the R1 to R4 are not hydrogen, halogen, or a polar functional group, at least one of a R1 and R2 coordination and a R3 and R4 coordination is bonded to each other to form an alkylidene group having 1 to 10 carbon atoms; or R1 or R2 is bonded to either R3 or R4 to form a saturated or unsaturated aliphatic ring having 4 to 12 carbon atoms or an aromatic ring having 6 to 24 carbon atoms,

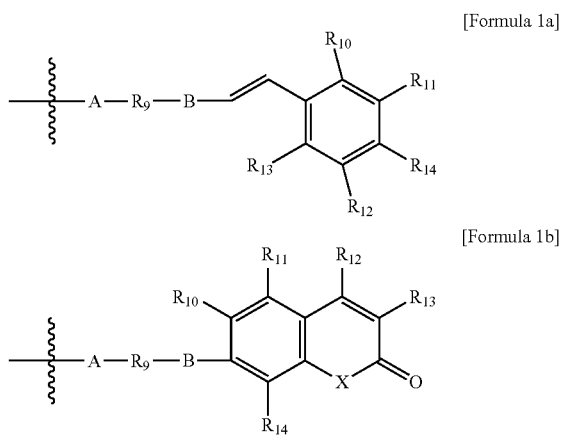

wherein A is chemical bond, oxygen, sulfur, or —NH—;
B is selected from the group consisting of chemical bond, substituted or unsubstituted alkylene having 1 to 20 carbon atoms, carbonyl, carboxy, ester, substituted or unsubstituted arylene having 6 to 40 carbon atoms, and substituted or unsubstituted heteroarylene having 6 to 40 carbon atoms;
X is oxygen or sulfur;
R9 is selected from the group consisting of chemical bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted aralkylene having 7 to 15 carbon atoms, and substituted or unsubstituted alkynylene having 2 to 20 carbon atoms;
at least one of R10 to R14 is a radical represented by -L-R15-R16-(substituted or unsubstituted C6-C40 aryl),
among the R10 to R14, the remainders other than the radical of -L-R15-R16-(substituted or unsubstituted C6-C40 aryl) are the same as or different from one another and independently selected from the group consisting of hydrogen; halogen; substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; and heteroaryl having 6 to 40 carbon atoms with a hetero element in Group 14, 15 or 16;

L is selected from the group consisting of oxygen, sulfur, —NH—, substituted or unsubstituted alkylene having 1 to 20 carbon atoms, carbonyl, carboxy, —CONH—, and substituted or unsubstituted arylene having 6 to 40 carbon atoms;

R15 is substituted or unsubstituted alkylene having 1 to 10 carbon atoms; and

R16 is selected from the group consisting of chemical bond, —O—, —C(=O)O—, —OC(=O)—, —NH—, —S—, and —C(=O)—.

2. The alignment layer as claimed in claim 1, wherein the radical of -L-R15-R16-(substituted or unsubstituted C6-C40 aryl) is represented by the following formula 2:

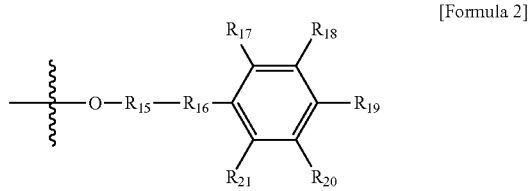

[Formula 2]

wherein R15 and R16 are as defined in formula 1a and 1b; and

R17 to R21 are the same as or different from one another and independently selected from the group consisting of hydrogen; halogen; substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; heteroaryl having 6 to 40 carbon atoms with a hetero element in Group 14, 15 or 16; and substituted or unsubstituted alkoxyaryl having 6 to 40 carbon atoms.

3. A liquid crystal retardation film comprising the alignment layer as claimed in claim 1, and a liquid crystal layer on the alignment layer.

4. A liquid crystal retardation film comprising the alignment layer as claimed in claim 2, and a liquid crystal layer on the alignment layer.

5. A display device comprising the alignment layer as claimed in claim 1.

6. A display device comprising the alignment layer as claimed in claim 2.

* * * * *

UNITED STATES PATENT AND TRADEMARK OFFICE
CERTIFICATE OF CORRECTION

PATENT NO. : 9,151,988 B2  
APPLICATION NO. : 14/567823  
DATED : October 6, 2015  
INVENTOR(S) : Dong-Woo Yoo Page 1 of 1

It is certified that error appears in the above-identified patent and that said Letters Patent is hereby corrected as shown below:

Title Page, below Item (65) insert

--(62) Related U.S. Application Data  
Division of application No. 13/244,089, filed on Sep. 23, 2011, now Pat. No. 8,946,366.--

Signed and Sealed this  
Twelfth Day of July, 2016

Michelle K. Lee  
*Director of the United States Patent and Trademark Office*